US009636068B2

(12) United States Patent
Yee et al.

(10) Patent No.: US 9,636,068 B2
(45) Date of Patent: May 2, 2017

(54) ANALYTE SENSOR AND APPARATUS FOR INSERTION OF THE SENSOR

(71) Applicant: ABBOTT DIABETES CARE INC., Alameda, CA (US)

(72) Inventors: Phillip Yee, San Francisco, CA (US); Christopher A. Thomas, San Leandro, CA (US); Udo Hoss, Castro Valley, CA (US); Lei He, Moraga, CA (US); Michael R. Love, Pleasanton, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

(21) Appl. No.: 15/192,531

(22) Filed: Jun. 24, 2016

(65) Prior Publication Data

US 2017/0020458 A1    Jan. 26, 2017

Related U.S. Application Data

(63) Continuation of application No. 12/698,129, filed on Feb. 1, 2010, now Pat. No. 9,402,544.

(60) Provisional application No. 61/149,639, filed on Feb. 3, 2009.

(51) Int. Cl.
| | |
|---|---|
| *A61B 5/00* | (2006.01) |
| *A61B 5/145* | (2006.01) |
| *A61M 5/158* | (2006.01) |
| *A61B 5/1486* | (2006.01) |

(52) U.S. Cl.
CPC .......... *A61B 5/6849* (2013.01); *A61B 5/0022* (2013.01); *A61B 5/14503* (2013.01); *A61B 5/14532* (2013.01); *A61B 5/14865* (2013.01); *A61B 5/742* (2013.01); *A61M 5/158* (2013.01); *A61B 2560/0214* (2013.01); *A61B 2560/0412* (2013.01)

(58) Field of Classification Search
CPC .......................... A61B 5/6849; A61B 5/14532
See application file for complete search history.

(56) References Cited

U.S. PATENT DOCUMENTS

| | | |
|---|---|---|
| 3,123,790 A | 3/1964 | Tyler |
| 3,260,656 A | 7/1966 | Ross, Jr. |
| 3,522,807 A | 8/1970 | Millenbach |
| 3,581,062 A | 5/1971 | Aston |
| 3,653,841 A | 4/1972 | Klein |
| 3,670,727 A | 6/1972 | Reiterman |
| 3,719,564 A | 3/1973 | Lilly, Jr. et al. |
| 3,776,832 A | 12/1973 | Oswin et al. |
| 3,837,339 A | 9/1974 | Aisenberg et al. |
| 3,926,760 A | 12/1975 | Allen et al. |

(Continued)

FOREIGN PATENT DOCUMENTS

| | | |
|---|---|---|
| CA | 2291105 | 12/1998 |
| DE | 4401400 | 7/1995 |

(Continued)

OTHER PUBLICATIONS

Aussedat, B., et al., "A User-Friendly Method for Calibrating a Subcutaneous Glucose Sensor-Based Hypoglycemic Alarm", Biosensors & Bioelectronics, vol. 12, No. 11, 1997, pp. 1061-1071.

(Continued)

*Primary Examiner* — Christian Jang
(74) *Attorney, Agent, or Firm* — One LLP

(57) ABSTRACT

An apparatus for insertion of a medical device in the skin of a subject is provided.

19 Claims, 29 Drawing Sheets

(56) References Cited

U.S. PATENT DOCUMENTS

| | | |
|---|---|---|
| 3,949,388 A | 4/1976 | Fuller |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,036,749 A | 7/1977 | Anderson |
| 4,055,175 A | 10/1977 | Clemens et al. |
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,120,292 A | 10/1978 | LeBlanc, Jr. et al. |
| 4,129,128 A | 12/1978 | McFarlane |
| 4,151,845 A | 5/1979 | Clemens |
| 4,168,205 A | 9/1979 | Danninger et al. |
| 4,172,770 A | 10/1979 | Semersky et al. |
| 4,178,916 A | 12/1979 | McNamara |
| 4,206,755 A | 6/1980 | Klein |
| 4,224,125 A | 9/1980 | Nakamura et al. |
| 4,240,438 A | 12/1980 | Updike et al. |
| 4,245,634 A | 1/1981 | Albisser et al. |
| 4,247,297 A | 1/1981 | Berti et al. |
| 4,294,258 A | 10/1981 | Bernard |
| 4,327,725 A | 5/1982 | Cortese et al. |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,356,074 A | 10/1982 | Johnson |
| 4,365,637 A | 12/1982 | Johnson |
| 4,366,033 A | 12/1982 | Richter et al. |
| 4,373,527 A | 2/1983 | Fischell |
| 4,375,399 A | 3/1983 | Havas et al. |
| 4,384,586 A | 5/1983 | Christiansen |
| 4,390,621 A | 6/1983 | Bauer |
| 4,401,122 A | 8/1983 | Clark, Jr. |
| 4,404,066 A | 9/1983 | Johnson |
| 4,418,148 A | 11/1983 | Oberhardt |
| 4,425,920 A | 1/1984 | Bourland et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,450,842 A | 5/1984 | Zick et al. |
| 4,458,686 A | 7/1984 | Clark, Jr. |
| 4,461,691 A | 7/1984 | Frank |
| 4,469,110 A | 9/1984 | Slama |
| 4,477,314 A | 10/1984 | Richter et al. |
| 4,478,976 A | 10/1984 | Goertz et al. |
| 4,484,987 A | 11/1984 | Gough |
| 4,494,950 A | 1/1985 | Fischell |
| 4,509,531 A | 4/1985 | Ward |
| 4,522,690 A | 6/1985 | Venkatasetty |
| 4,524,114 A | 6/1985 | Samuels et al. |
| 4,526,661 A | 7/1985 | Steckhan et al. |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,560,534 A | 12/1985 | Kung et al. |
| 4,571,292 A | 2/1986 | Liu et al. |
| 4,573,994 A | 3/1986 | Fischell et al. |
| 4,581,336 A | 4/1986 | Malloy et al. |
| 4,595,011 A | 6/1986 | Phillips |
| 4,619,754 A | 10/1986 | Niki et al. |
| 4,619,793 A | 10/1986 | Lee |
| 4,627,445 A | 12/1986 | Garcia et al. |
| 4,627,842 A | 12/1986 | Katz |
| 4,627,908 A | 12/1986 | Miller |
| 4,633,878 A | 1/1987 | Bombardieri |
| 4,637,403 A | 1/1987 | Garcia et al. |
| 4,650,547 A | 3/1987 | Gough |
| 4,654,197 A | 3/1987 | Lilja et al. |
| 4,655,880 A | 4/1987 | Liu |
| 4,655,885 A | 4/1987 | Hill et al. |
| 4,671,288 A | 6/1987 | Gough |
| 4,679,562 A | 7/1987 | Luksha |
| 4,680,268 A | 7/1987 | Clark, Jr. |
| 4,682,602 A | 7/1987 | Prohaska |
| 4,684,537 A | 8/1987 | Graetzel et al. |
| 4,685,463 A | 8/1987 | Williams |
| 4,685,466 A | 8/1987 | Rau |
| 4,698,057 A | 10/1987 | Joishy |
| 4,703,756 A | 11/1987 | Gough et al. |
| 4,711,245 A | 12/1987 | Higgins et al. |
| 4,711,247 A | 12/1987 | Fishman |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,729,672 A | 3/1988 | Takagi |
| 4,731,726 A | 3/1988 | Allen, III |
| 4,749,985 A | 6/1988 | Corsberg |
| 4,755,173 A | 7/1988 | Konopka |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,777,953 A | 10/1988 | Ash et al. |
| 4,779,618 A | 10/1988 | Mund et al. |
| 4,781,798 A | 11/1988 | Gough |
| 4,784,736 A | 11/1988 | Lonsdale et al. |
| 4,795,707 A | 1/1989 | Niiyama et al. |
| 4,796,634 A | 1/1989 | Huntsman et al. |
| 4,805,624 A | 2/1989 | Yao et al. |
| 4,813,424 A | 3/1989 | Wilkins |
| 4,815,469 A | 3/1989 | Cohen et al. |
| 4,820,399 A | 4/1989 | Senda et al. |
| 4,822,337 A | 4/1989 | Newhouse et al. |
| 4,830,959 A | 5/1989 | McNeil et al. |
| 4,832,797 A | 5/1989 | Vadgama et al. |
| RE32,947 E | 6/1989 | Dormer et al. |
| 4,840,893 A | 6/1989 | Hill et al. |
| 4,848,351 A | 7/1989 | Finch |
| 4,854,322 A | 8/1989 | Ash et al. |
| 4,871,351 A | 10/1989 | Feingold |
| 4,871,440 A | 10/1989 | Nagata et al. |
| 4,874,500 A | 10/1989 | Madou et al. |
| 4,890,620 A | 1/1990 | Gough |
| 4,894,137 A | 1/1990 | Takizawa et al. |
| 4,895,147 A | 1/1990 | Bodicky et al. |
| 4,897,162 A | 1/1990 | Lewandowski et al. |
| 4,897,173 A | 1/1990 | Nankai et al. |
| 4,909,908 A | 3/1990 | Ross et al. |
| 4,911,794 A | 3/1990 | Parce et al. |
| 4,917,800 A | 4/1990 | Lonsdale et al. |
| 4,919,141 A | 4/1990 | Zier et al. |
| 4,919,767 A | 4/1990 | Vadgama et al. |
| 4,921,199 A | 5/1990 | Villaveces |
| 4,923,586 A | 5/1990 | Katayama et al. |
| 4,925,268 A | 5/1990 | Iyer et al. |
| 4,927,516 A | 5/1990 | Yamaguchi et al. |
| 4,934,369 A | 6/1990 | Maxwell |
| 4,935,105 A | 6/1990 | Churchouse |
| 4,935,345 A | 6/1990 | Guilbeau et al. |
| 4,938,860 A | 7/1990 | Wogoman |
| 4,944,299 A | 7/1990 | Silvian |
| 4,950,378 A | 8/1990 | Nagata |
| 4,953,552 A | 9/1990 | DeMarzo |
| 4,954,129 A | 9/1990 | Giuliani et al. |
| 4,969,468 A | 11/1990 | Byers et al. |
| 4,970,145 A | 11/1990 | Bennetto et al. |
| 4,974,929 A | 12/1990 | Curry |
| 4,986,271 A | 1/1991 | Wilkins |
| 4,988,341 A | 1/1991 | Columbus et al. |
| 4,994,167 A | 2/1991 | Shults et al. |
| 4,995,402 A | 2/1991 | Smith et al. |
| 5,000,180 A | 3/1991 | Kuypers et al. |
| 5,001,054 A | 3/1991 | Wagner |

(56) References Cited

U.S. PATENT DOCUMENTS

| | | |
|---|---|---|
| 5,013,161 A | 5/1991 | Zaragoza et al. |
| 5,019,974 A | 5/1991 | Beckers |
| 5,035,860 A | 7/1991 | Kleingeld et al. |
| 5,036,860 A | 8/1991 | Leigh et al. |
| 5,047,044 A | 9/1991 | Smith et al. |
| 5,050,612 A | 9/1991 | Matsumura |
| 5,055,171 A | 10/1991 | Peck |
| 5,058,592 A | 10/1991 | Whisler |
| 5,070,535 A | 12/1991 | Hochmair et al. |
| 5,082,550 A | 1/1992 | Rishpon et al. |
| 5,082,786 A | 1/1992 | Nakamoto |
| 5,089,112 A | 2/1992 | Skotheim et al. |
| 5,095,904 A | 3/1992 | Seligman et al. |
| 5,101,814 A | 4/1992 | Palti |
| 5,106,365 A | 4/1992 | Hernandez |
| 5,108,564 A | 4/1992 | Szuminsky et al. |
| 5,108,889 A | 4/1992 | Smith et al. |
| 5,109,850 A | 5/1992 | Blanco et al. |
| 5,120,420 A | 6/1992 | Nankai et al. |
| 5,122,925 A | 6/1992 | Inpyn |
| 5,126,034 A | 6/1992 | Carter et al. |
| 5,133,856 A | 7/1992 | Yamaguchi et al. |
| 5,135,003 A | 8/1992 | Souma |
| 5,140,985 A | 8/1992 | Schroeder et al. |
| 5,141,868 A | 8/1992 | Shanks et al. |
| 5,161,532 A | 11/1992 | Joseph |
| 5,165,407 A | 11/1992 | Wilson et al. |
| 5,174,291 A | 12/1992 | Schoonen et al. |
| 5,190,041 A | 3/1993 | Palti |
| 5,192,416 A | 3/1993 | Wang et al. |
| 5,198,367 A | 3/1993 | Aizawa et al. |
| 5,202,261 A | 4/1993 | Musho et al. |
| 5,205,920 A | 4/1993 | Oyama et al. |
| 5,208,154 A | 5/1993 | Weaver et al. |
| 5,209,229 A | 5/1993 | Gilli |
| 5,217,595 A | 6/1993 | Smith et al. |
| 5,229,282 A | 7/1993 | Yoshioka et al. |
| 5,234,835 A | 8/1993 | Nestor et al. |
| 5,238,729 A | 8/1993 | Debe |
| 5,246,867 A | 9/1993 | Lakowicz et al. |
| 5,250,439 A | 10/1993 | Musho et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,264,106 A | 11/1993 | McAleer et al. |
| 5,271,815 A | 12/1993 | Wong |
| 5,279,294 A | 1/1994 | Anderson et al. |
| 5,284,156 A | 2/1994 | Schramm et al. |
| 5,285,792 A | 2/1994 | Sjoquist et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,293,546 A | 3/1994 | Tadros et al. |
| 5,293,877 A | 3/1994 | O'Hara et al. |
| 5,299,571 A | 4/1994 | Mastrototaro |
| 5,320,098 A | 6/1994 | Davidson |
| 5,320,725 A | 6/1994 | Gregg et al. |
| 5,322,063 A | 6/1994 | Allen et al. |
| 5,337,747 A | 8/1994 | Neftel |
| 5,340,722 A | 8/1994 | Wolfbeis et al. |
| 5,342,789 A | 8/1994 | Chick et al. |
| 5,352,348 A | 10/1994 | Young et al. |
| 5,356,786 A | 10/1994 | Heller et al. |
| 5,360,404 A | 11/1994 | Novacek et al. |
| 5,368,028 A | 11/1994 | Palti |
| 5,372,133 A | 12/1994 | Hogen Esch |
| 5,372,427 A | 12/1994 | Padovani et al. |
| 5,376,251 A | 12/1994 | Kaneko et al. |
| 5,378,628 A | 1/1995 | Gratzel et al. |
| 5,379,238 A | 1/1995 | Stark |
| 5,387,327 A | 2/1995 | Khan |
| 5,390,671 A | 2/1995 | Lord et al. |
| 5,391,250 A | 2/1995 | Cheney, II et al. |
| 5,395,504 A | 3/1995 | Saurer et al. |
| 5,400,782 A | 3/1995 | Beaubiah |
| 5,408,999 A | 4/1995 | Singh et al. |
| 5,411,647 A | 5/1995 | Johnson et al. |
| 5,425,361 A | 6/1995 | Fenzlein et al. |
| 5,431,160 A | 7/1995 | Wilkins |
| 5,431,921 A | 7/1995 | Thombre |
| 5,437,999 A | 8/1995 | Diebold et al. |
| 5,462,645 A | 10/1995 | Albery et al. |
| 5,469,846 A | 11/1995 | Khan |
| 5,472,317 A | 12/1995 | Field et al. |
| 5,489,414 A | 2/1996 | Schreiber et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,545,191 A | 8/1996 | Mann et al. |
| 5,549,568 A | 8/1996 | Shields |
| 5,551,427 A | 9/1996 | Altman |
| 5,560,357 A | 10/1996 | Faupei et al. |
| 5,562,713 A | 10/1996 | Silvian |
| 5,565,085 A | 10/1996 | Ikeda et al. |
| 5,567,302 A | 10/1996 | Song et al. |
| 5,568,806 A | 10/1996 | Cheney, II et al. |
| 5,569,186 A | 10/1996 | Lord et al. |
| 5,575,563 A | 11/1996 | Chiu et al. |
| 5,582,184 A | 12/1996 | Erickson et al. |
| 5,582,697 A | 12/1996 | Ikeda et al. |
| 5,582,698 A | 12/1996 | Flaherty et al. |
| 5,584,813 A | 12/1996 | Livingston et al. |
| 5,586,553 A | 12/1996 | Halli et al. |
| 5,589,326 A | 12/1996 | Deng et al. |
| 5,593,852 A | 1/1997 | Heller et al. |
| 5,596,150 A | 1/1997 | Arndt et al. |
| 5,601,435 A | 2/1997 | Quy |
| 5,609,575 A | 3/1997 | Larson et al. |
| 5,617,851 A | 4/1997 | Lipkovker |
| 5,628,310 A | 5/1997 | Rao et al. |
| 5,628,890 A | 5/1997 | Carter et al. |
| 5,632,557 A | 5/1997 | Simons |
| 5,651,869 A | 7/1997 | Yoshioka et al. |
| 5,653,239 A | 8/1997 | Pompei et al. |
| 5,660,163 A | 8/1997 | Schulman et al. |
| 5,665,222 A | 9/1997 | Heller et al. |
| 5,670,031 A | 9/1997 | Hintsche et al. |
| 5,680,858 A | 10/1997 | Hansen et al. |
| 5,682,233 A | 10/1997 | Brinda |
| 5,695,623 A | 12/1997 | Michel et al. |
| 5,708,247 A | 1/1998 | McAleer et al. |
| 5,711,001 A | 1/1998 | Bussan et al. |
| 5,711,297 A | 1/1998 | Iliff |
| 5,711,861 A | 1/1998 | Ward et al. |
| 5,711,862 A | 1/1998 | Sakoda et al. |
| 5,733,044 A | 3/1998 | Rose et al. |
| 5,735,285 A | 4/1998 | Albert et al. |
| 5,741,211 A | 4/1998 | Reniric et al. |
| 5,749,656 A | 5/1998 | Boehm et al. |
| 5,766,131 A | 6/1998 | Kondo et al. |
| 5,771,001 A | 6/1998 | Cobb |
| 5,772,586 A | 6/1998 | Heinonen et al. |
| 5,779,665 A | 7/1998 | Mastrototaro et al. |
| 5,791,344 A | 8/1998 | Schulman et al. |
| 5,800,420 A | 9/1998 | Gross et al. |
| 5,807,375 A | 9/1998 | Gross et al. |
| 5,814,020 A | 9/1998 | Gross |
| 5,820,551 A | 10/1998 | Hill et al. |
| 5,820,622 A | 10/1998 | Gross et al. |
| 5,822,715 A | 10/1998 | Worthington et al. |
| 5,827,184 A | 10/1998 | Netherly et al. |
| 5,840,020 A | 11/1998 | Heinonen et al. |
| 5,842,983 A | 12/1998 | Abel et al. |
| 5,851,197 A | 12/1998 | Marano et al. |
| 5,858,001 A | 1/1999 | Tsals et al. |
| 5,865,804 A | 2/1999 | Bachynsky |
| 5,885,211 A | 3/1999 | Eppstein et al. |

(56) References Cited

U.S. PATENT DOCUMENTS

| | | |
|---|---|---|
| 5,899,855 A | 5/1999 | Brown |
| 5,924,979 A | 7/1999 | Swedlow et al. |
| 5,925,021 A | 7/1999 | Castellano et al. |
| 5,931,814 A | 8/1999 | Alex et al. |
| 5,948,006 A | 9/1999 | Mann |
| 5,951,521 A | 9/1999 | Mastrototaro et al. |
| 5,954,643 A | 9/1999 | Van Antwerp |
| 5,954,685 A | 9/1999 | Tierney |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,972,199 A | 10/1999 | Heller et al. |
| 5,987,353 A | 11/1999 | Khatchatrian et al. |
| 5,993,411 A | 11/1999 | Choi |
| 5,995,860 A | 11/1999 | Sun et al. |
| 5,997,501 A | 12/1999 | Gross et al. |
| 6,001,067 A | 12/1999 | Shults et al. |
| 6,004,278 A | 12/1999 | Botich et al. |
| 6,022,368 A | 2/2000 | Gavronsky et al. |
| 6,024,699 A | 2/2000 | Surwit et al. |
| 6,026,321 A | 2/2000 | Miyata et al. |
| 6,027,459 A | 2/2000 | Shain et al. |
| 6,049,727 A | 4/2000 | Crothall |
| 6,056,718 A | 5/2000 | Funderburk et al. |
| 6,068,399 A | 5/2000 | Tseng |
| 6,083,710 A | 7/2000 | Heller et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,093,172 A | 7/2000 | Funderburk et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,143,164 A | 11/2000 | Heller et al. |
| 6,159,147 A | 12/2000 | Lichter et al. |
| 6,162,611 A | 12/2000 | Heller et al. |
| 6,175,752 B1 | 1/2001 | Say et al. |
| 6,186,982 B1 | 2/2001 | Gross et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,248,067 B1 | 6/2001 | Causey, III et al. |
| 6,254,536 B1 | 7/2001 | DeVito |
| 6,254,586 B1 | 7/2001 | Mann et al. |
| 6,275,717 B1 | 8/2001 | Gross et al. |
| 6,283,761 B1 | 9/2001 | Joao |
| 6,283,982 B1 | 9/2001 | Levaughn et al. |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,331,244 B1 | 12/2001 | Lewis et al. |
| 6,338,790 B1 | 1/2002 | Feldman et al. |
| 6,348,640 B1 | 2/2002 | Navot et al. |
| 6,359,444 B1 | 3/2002 | Grimes |
| 6,360,888 B1 | 3/2002 | McIvor et al. |
| 6,366,794 B1 | 4/2002 | Moussy et al. |
| 6,368,141 B1 | 4/2002 | Van Antwerp et al. |
| 6,368,274 B1 | 4/2002 | Van Antwerp et al. |
| 6,377,828 B1 | 4/2002 | Chaiken et al. |
| 6,379,301 B1 | 4/2002 | Worthington et al. |
| 6,409,740 B1 | 6/2002 | Kuhr et al. |
| 6,418,332 B1 | 7/2002 | Mastrototaro et al. |
| 6,424,847 B1 | 7/2002 | Mastrototaro et al. |
| 6,427,088 B1 | 7/2002 | Bowman, IV et al. |
| 6,437,679 B1 | 8/2002 | Roques |
| 6,440,068 B1 | 8/2002 | Brown et al. |
| 6,445,374 B2 | 9/2002 | Albert et al. |
| 6,478,736 B1 | 11/2002 | Mault |
| 6,482,176 B1 | 11/2002 | Wich |
| 6,484,045 B1 | 11/2002 | Holker et al. |
| 6,484,046 B1 | 11/2002 | Say et al. |
| 6,514,718 B2 | 2/2003 | Heller et al. |
| 6,520,326 B2 | 2/2003 | McIvor et al. |
| 6,522,927 B1 | 2/2003 | Bishay et al. |
| 6,551,494 B1 | 4/2003 | Heller et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,566 B2 | 6/2003 | Effenhauser |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,589,229 B1 | 7/2003 | Connelly et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,676,290 B1 | 1/2004 | Lu |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,699,188 B2 | 3/2004 | Wessel |
| 6,702,857 B2 | 3/2004 | Brauker et al. |
| 6,733,446 B2 | 5/2004 | Lebel et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,830,551 B1 | 12/2004 | Uchigaki et al. |
| 6,837,858 B2 | 1/2005 | Cunningham et al. |
| 6,837,988 B2 | 1/2005 | Leong et al. |
| 6,849,052 B2 | 2/2005 | Uchigaki et al. |
| 6,854,882 B2 | 2/2005 | Chen |
| 6,862,465 B2 | 3/2005 | Shults et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,895,265 B2 | 5/2005 | Silver |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman, IV et al. |
| 6,958,705 B2 | 10/2005 | Lebel et al. |
| 6,959,211 B2 | 10/2005 | Rule et al. |
| 6,968,294 B2 | 11/2005 | Gutta et al. |
| 6,971,274 B2 | 12/2005 | Olin |
| 6,971,999 B2 | 12/2005 | Py et al. |
| 6,974,437 B2 | 12/2005 | Lebel et al. |
| 6,990,366 B2 | 1/2006 | Say et al. |
| 6,997,907 B2 | 2/2006 | Safabash et al. |

(56) References Cited

U.S. PATENT DOCUMENTS

| | | |
|---|---|---|
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,024,245 B2 | 4/2006 | Lebel et al. |
| 7,025,743 B2 | 4/2006 | Mann et al. |
| 7,041,068 B2 | 5/2006 | Freeman et al. |
| 7,041,468 B2 | 5/2006 | Drucker et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,097,637 B2 | 8/2006 | Triplett et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,134,999 B2 | 11/2006 | Brauker et al. |
| 7,136,689 B2 | 11/2006 | Shults et al. |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,207,974 B2 | 4/2007 | Safabash et al. |
| 7,226,978 B2 | 6/2007 | Tapsak et al. |
| 7,276,029 B2 | 10/2007 | Goode, Jr. et al. |
| 7,278,983 B2 | 10/2007 | Ireland et al. |
| 7,297,151 B2 | 11/2007 | Boecker et al. |
| 7,299,082 B2 | 11/2007 | Feldman et al. |
| 7,310,544 B2 | 12/2007 | Brister et al. |
| 7,318,816 B2 | 1/2008 | Bobroff et al. |
| 7,324,012 B2 | 1/2008 | Mann et al. |
| 7,329,239 B2 | 2/2008 | Safabash et al. |
| 7,335,294 B2 | 2/2008 | Heller et al. |
| 7,340,309 B2 | 3/2008 | Miazga et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,402,153 B2 | 7/2008 | Steil et al. |
| 7,416,541 B2 | 8/2008 | Yuzhakov et al. |
| 7,424,318 B2 | 9/2008 | Brister et al. |
| 7,455,663 B2 | 11/2008 | Bikovsky |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,604,592 B2 | 10/2009 | Freeman et al. |
| 7,613,491 B2 | 11/2009 | Boock et al. |
| 7,615,007 B2 | 11/2009 | Shults et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,666,149 B2 | 2/2010 | Simons et al. |
| 7,697,967 B2 | 4/2010 | Stafford |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,147 B1 | 6/2010 | Osorio et al. |
| 7,731,657 B2 | 6/2010 | Stafford |
| 7,736,344 B2 | 6/2010 | Moberg et al. |
| 7,763,042 B2 | 7/2010 | Iio et al. |
| 7,822,454 B1 | 10/2010 | Alden et al. |
| 2001/0056262 A1 | 12/2001 | Cabiri et al. |
| 2002/0013538 A1 | 1/2002 | Teller |
| 2002/0019022 A1 | 2/2002 | Dunn et al. |
| 2002/0019606 A1 | 2/2002 | Lebel et al. |
| 2002/0022855 A1 | 2/2002 | Bobroff et al. |
| 2002/0023852 A1 | 2/2002 | McIvor et al. |
| 2002/0042090 A1 | 4/2002 | Heller et al. |
| 2002/0055711 A1 | 5/2002 | Lavi et al. |
| 2002/0082487 A1 | 6/2002 | Kollias et al. |
| 2002/0103499 A1 | 8/2002 | Perez et al. |
| 2002/0106709 A1 | 8/2002 | Potts et al. |
| 2002/0119711 A1 | 8/2002 | VanAntwerp et al. |
| 2002/0128594 A1 | 9/2002 | Das et al. |
| 2002/0130042 A1 | 9/2002 | Moerman et al. |
| 2002/0154050 A1 | 10/2002 | Krupp et al. |
| 2002/0161288 A1 | 10/2002 | Shin et al. |
| 2002/0165462 A1 | 11/2002 | Westbrook et al. |
| 2002/0169369 A1 | 11/2002 | Ward et al. |
| 2002/0198444 A1 | 12/2002 | Uchigaki et al. |
| 2003/0023317 A1 | 1/2003 | Brauker et al. |
| 2003/0023461 A1 | 1/2003 | Quintanilla et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0060753 A1 | 3/2003 | Starkweather et al. |
| 2003/0065308 A1 | 4/2003 | Lebel et al. |
| 2003/0069510 A1 | 4/2003 | Semler |
| 2003/0078481 A1 | 4/2003 | McIvor et al. |
| 2003/0078560 A1 | 4/2003 | Miller et al. |
| 2003/0097092 A1 | 5/2003 | Flaherty |
| 2003/0100040 A1 | 5/2003 | Bonnecaze et al. |
| 2003/0109775 A1 | 6/2003 | O'Neil et al. |
| 2003/0134347 A1 | 7/2003 | Heller et al. |
| 2003/0135333 A1 | 7/2003 | Aceti et al. |
| 2003/0144581 A1 | 7/2003 | Conn et al. |
| 2003/0144608 A1 | 7/2003 | Kojima et al. |
| 2003/0155656 A1 | 8/2003 | Chiu et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0199790 A1 | 10/2003 | Boecker et al. |
| 2003/0199910 A1 | 10/2003 | Boecker et al. |
| 2003/0212379 A1 | 11/2003 | Bylund et al. |
| 2003/0217966 A1 | 11/2003 | Tapsak et al. |
| 2003/0225361 A1 | 12/2003 | Sabra |
| 2004/0002682 A1 | 1/2004 | Kovelman et al. |
| 2004/0010207 A1 | 1/2004 | Flaherty et al. |
| 2004/0011671 A1 | 1/2004 | Shults et al. |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0064068 A1 | 4/2004 | DeNuzzio et al. |
| 2004/0064133 A1 | 4/2004 | Miller et al. |
| 2004/0096959 A1 | 5/2004 | Stiene et al. |
| 2004/0106858 A1 | 6/2004 | Say et al. |
| 2004/0106859 A1 | 6/2004 | Say et al. |
| 2004/0116847 A1 | 6/2004 | Wall |
| 2004/0116866 A1 | 6/2004 | Gorman et al. |
| 2004/0122353 A1 | 6/2004 | Shahmirian et al. |
| 2004/0122489 A1 | 6/2004 | Mazar et al. |
| 2004/0133164 A1 | 7/2004 | Funderburk et al. |
| 2004/0135684 A1 | 7/2004 | Steinthal et al. |
| 2004/0138544 A1 | 7/2004 | Ward et al. |
| 2004/0138588 A1 | 7/2004 | Saikley et al. |
| 2004/0138688 A1 | 7/2004 | Giraud |
| 2004/0147996 A1 | 7/2004 | Miazga et al. |
| 2004/0152622 A1 | 8/2004 | Keith et al. |
| 2004/0158207 A1 | 8/2004 | Hunn et al. |
| 2004/0167801 A1 | 8/2004 | Say et al. |
| 2004/0171910 A1 | 9/2004 | Moore-Steele |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193090 A1 | 9/2004 | Lebel et al. |
| 2004/0199059 A1 | 10/2004 | Brauker et al. |
| 2004/0204687 A1 | 10/2004 | Mogensen et al. |
| 2004/0223985 A1 | 11/2004 | Dunfield et al. |
| 2004/0225338 A1 | 11/2004 | Lebel et al. |
| 2004/0236200 A1 | 11/2004 | Say et al. |
| 2004/0236251 A1 | 11/2004 | Roe et al. |
| 2004/0254433 A1 | 12/2004 | Bandis et al. |

(56) References Cited

U.S. PATENT DOCUMENTS

| | | |
|---|---|---|
| 2004/0254434 A1 | 12/2004 | Goodnow et al. |
| 2004/0267300 A1 | 12/2004 | Mace |
| 2005/0003470 A1 | 1/2005 | Nelson et al. |
| 2005/0004494 A1 | 1/2005 | Perez et al. |
| 2005/0010269 A1 | 1/2005 | Lebel et al. |
| 2005/0027177 A1 | 2/2005 | Shin et al. |
| 2005/0027180 A1 | 2/2005 | Goode, Jr. et al. |
| 2005/0031689 A1 | 2/2005 | Shults et al. |
| 2005/0043598 A1 | 2/2005 | Goode, Jr. et al. |
| 2005/0070819 A1 | 3/2005 | Poux et al. |
| 2005/0085872 A1 | 4/2005 | Yanagihara et al. |
| 2005/0090607 A1 | 4/2005 | Tapsak et al. |
| 2005/0090850 A1 | 4/2005 | Thoes et al. |
| 2005/0106713 A1 | 5/2005 | Phan et al. |
| 2005/0112169 A1 | 5/2005 | Brauker et al. |
| 2005/0114068 A1 | 5/2005 | Chey et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0154410 A1 | 7/2005 | Conway et al. |
| 2005/0165404 A1 | 7/2005 | Miller |
| 2005/0173245 A1 | 8/2005 | Feldman et al. |
| 2005/0176136 A1 | 8/2005 | Burd et al. |
| 2005/0182306 A1 | 8/2005 | Sloan |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0197554 A1 | 9/2005 | Polcha |
| 2005/0199494 A1 | 9/2005 | Say et al. |
| 2005/0203360 A1 | 9/2005 | Brauker et al. |
| 2005/0222518 A1 | 10/2005 | Dib |
| 2005/0222599 A1 | 10/2005 | Czernecki et al. |
| 2005/0236277 A9 | 10/2005 | Imran et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245844 A1 | 11/2005 | Mace et al. |
| 2005/0277164 A1 | 12/2005 | Drucker et al. |
| 2005/0283114 A1 | 12/2005 | Bresina et al. |
| 2005/0287620 A1 | 12/2005 | Heller et al. |
| 2006/0001538 A1 | 1/2006 | Kraft et al. |
| 2006/0004303 A1 | 1/2006 | Weidenhaupt et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0047220 A1 | 3/2006 | Sakata et al. |
| 2006/0081469 A1 | 4/2006 | Lee |
| 2006/0129173 A1 | 6/2006 | Wilkinson |
| 2006/0155210 A1 | 7/2006 | Beckman et al. |
| 2006/0155317 A1 | 7/2006 | List |
| 2006/0166629 A1 | 7/2006 | Reggiardo |
| 2006/0173444 A1 | 8/2006 | Choy et al. |
| 2006/0189863 A1 | 8/2006 | Peyser et al. |
| 2006/0189939 A1 | 8/2006 | Gonnelli et al. |
| 2006/0195029 A1 | 8/2006 | Shults et al. |
| 2006/0200970 A1 | 9/2006 | Brister et al. |
| 2006/0222566 A1 | 10/2006 | Brauker et al. |
| 2006/0224171 A1 | 10/2006 | Sakata et al. |
| 2006/0226985 A1 | 10/2006 | Goodnow et al. |
| 2006/0247508 A1 | 11/2006 | Fennell |
| 2006/0258929 A1 | 11/2006 | Goode, Jr. et al. |
| 2006/0264888 A1 | 11/2006 | Moberg et al. |
| 2006/0276724 A1 | 12/2006 | Freeman et al. |
| 2007/0016381 A1 | 1/2007 | Kamath et al. |
| 2007/0027381 A1 | 2/2007 | Stafford |
| 2007/0038044 A1 | 2/2007 | Dobbles et al. |
| 2007/0060814 A1 | 3/2007 | Stafford |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0106135 A1 | 5/2007 | Sloan et al. |
| 2007/0110124 A1 | 5/2007 | Shiraki et al. |
| 2007/0123819 A1 | 5/2007 | Mernoe et al. |
| 2007/0149875 A1 | 6/2007 | Ouyang et al. |
| 2007/0156094 A1 | 7/2007 | Safabash et al. |
| 2007/0163880 A1 | 7/2007 | Woo et al. |
| 2007/0173706 A1 | 7/2007 | Neinast et al. |
| 2007/0173741 A1 | 7/2007 | Deshmukh et al. |
| 2007/0191701 A1 | 8/2007 | Feldman et al. |
| 2007/0203407 A1 | 8/2007 | Hoss et al. |
| 2007/0203966 A1 | 8/2007 | Brauker et al. |
| 2007/0213611 A1 | 9/2007 | Simpson et al. |
| 2007/0235331 A1 | 10/2007 | Simpson et al. |
| 2007/0244368 A1 | 10/2007 | Bayloff et al. |
| 2007/0244398 A1 | 10/2007 | Lo et al. |
| 2007/0249922 A1 | 10/2007 | Peyser et al. |
| 2007/0255302 A1 | 11/2007 | Koeppel et al. |
| 2008/0004512 A1 | 1/2008 | Funderburk et al. |
| 2008/0004573 A1 | 1/2008 | Kaufmann et al. |
| 2008/0009692 A1 | 1/2008 | Stafford |
| 2008/0009805 A1 | 1/2008 | Ethelfeld |
| 2008/0017522 A1 | 1/2008 | Heller et al. |
| 2008/0021666 A1 | 1/2008 | Goode, Jr. et al. |
| 2008/0027474 A1 | 1/2008 | Curry et al. |
| 2008/0029391 A1 | 2/2008 | Mao et al. |
| 2008/0033254 A1 | 2/2008 | Kamath et al. |
| 2008/0033268 A1 | 2/2008 | Stafford |
| 2008/0033318 A1 | 2/2008 | Mace et al. |
| 2008/0039702 A1 | 2/2008 | Hayter et al. |
| 2008/0045824 A1 | 2/2008 | Tapsak et al. |
| 2008/0064937 A1 | 3/2008 | McGarraugh et al. |
| 2008/0064941 A1 | 3/2008 | Funderburk et al. |
| 2008/0065646 A1 | 3/2008 | Zhang et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097246 A1 | 4/2008 | Stafford |
| 2008/0108942 A1 | 5/2008 | Brister et al. |
| 2008/0112848 A1 | 5/2008 | Huffstodt et al. |
| 2008/0114280 A1 | 5/2008 | Stafford |
| 2008/0119707 A1 | 5/2008 | Stafford |
| 2008/0133702 A1 | 6/2008 | Sharma et al. |
| 2008/0154205 A1 | 6/2008 | Wojcik |
| 2008/0167578 A1 | 7/2008 | Bryer et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195049 A1 | 8/2008 | Thalmann et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200897 A1 | 8/2008 | Hoss et al. |
| 2008/0208025 A1 | 8/2008 | Shults et al. |
| 2008/0214915 A1 | 9/2008 | Brister et al. |
| 2008/0214918 A1 | 9/2008 | Brister et al. |

(56) References Cited

U.S. PATENT DOCUMENTS

| | | |
|---|---|---|
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0262469 A1 | 10/2008 | Brister et al. |
| 2008/0269673 A1 | 10/2008 | Butoi et al. |
| 2008/0275313 A1 | 11/2008 | Brister et al. |
| 2008/0283396 A1 | 11/2008 | Wang et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0294096 A1 | 11/2008 | Uber et al. |
| 2008/0296155 A1 | 12/2008 | Shults et al. |
| 2008/0300476 A1 | 12/2008 | Stafford |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0005659 A1 | 1/2009 | Kollias et al. |
| 2009/0012377 A1 | 1/2009 | Jennewine et al. |
| 2009/0012379 A1 | 1/2009 | Goode, Jr. et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0036915 A1 | 2/2009 | Karbowniczek et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0054866 A1 | 2/2009 | Teisen-Simony et al. |
| 2009/0062633 A1 | 3/2009 | Brauker et al. |
| 2009/0062635 A1 | 3/2009 | Brauker et al. |
| 2009/0069658 A1 | 3/2009 | Say et al. |
| 2009/0069750 A1 | 3/2009 | Schraga |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0088614 A1 | 4/2009 | Taub |
| 2009/0088787 A1 | 4/2009 | Koike et al. |
| 2009/0099436 A1 | 4/2009 | Brister et al. |
| 2009/0102678 A1 | 4/2009 | Mazza et al. |
| 2009/0105569 A1 | 4/2009 | Stafford |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0124979 A1 | 5/2009 | Raymond et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielsen |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0171182 A1 | 7/2009 | Stafford |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198215 A1 | 8/2009 | Chong et al. |
| 2009/0203981 A1 | 8/2009 | Brauker et al. |
| 2009/0204341 A1 | 8/2009 | Brauker et al. |
| 2009/0212766 A1 | 8/2009 | Olson et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0259118 A1 | 10/2009 | Feldman et al. |
| 2009/0270765 A1 | 10/2009 | Ghesquiere et al. |
| 2009/0287073 A1 | 11/2009 | Boock et al. |
| 2009/0287074 A1 | 11/2009 | Shults et al. |
| 2009/0292184 A1 | 11/2009 | Funderburk et al. |
| 2009/0292185 A1 | 11/2009 | Funderburk et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299167 A1 | 12/2009 | Seymour |
| 2009/0299276 A1 | 12/2009 | Brauker et al. |
| 2010/0004597 A1 | 1/2010 | Gyrn et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049014 A1 | 2/2010 | Funderburk et al. |
| 2010/0049024 A1 | 2/2010 | Saint et al. |
| 2010/0063373 A1 | 3/2010 | Kamath et al. |
| 2010/0069728 A1 | 3/2010 | Funderburk et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0100113 A1 | 4/2010 | Iio et al. |
| 2010/0113897 A1 | 5/2010 | Brenneman et al. |
| 2010/0119693 A1 | 5/2010 | Tapsak et al. |
| 2010/0121169 A1 | 5/2010 | Petisce et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode et al. |
| 2010/0179401 A1 | 7/2010 | Rasdal et al. |
| 2010/0179402 A1 | 7/2010 | Goode, Jr. et al. |
| 2010/0179404 A1 | 7/2010 | Kamath et al. |
| 2010/0179408 A1 | 7/2010 | Kamath et al. |
| 2010/0179409 A1 | 7/2010 | Kamath et al. |
| 2010/0185065 A1 | 7/2010 | Goode, Jr. et al. |
| 2010/0185069 A1 | 7/2010 | Brister et al. |
| 2010/0185070 A1 | 7/2010 | Brister et al. |
| 2010/0185071 A1 | 7/2010 | Simpson et al. |
| 2010/0185072 A1 | 7/2010 | Goode, Jr. et al. |
| 2010/0185075 A1 | 7/2010 | Brister et al. |
| 2010/0191082 A1 | 7/2010 | Brister et al. |
| 2010/0198033 A1 | 8/2010 | Krulevitch et al. |
| 2010/0198034 A1 | 8/2010 | Thomas et al. |
| 2010/0198035 A1 | 8/2010 | Kamath et al. |
| 2010/0198036 A1 | 8/2010 | Kamath et al. |
| 2010/0204653 A1 | 8/2010 | Gyrn et al. |

(56) References Cited

U.S. PATENT DOCUMENTS

| | | |
|---|---|---|
| 2010/0212583 A1 | 8/2010 | Brister et al. |
| 2010/0214104 A1 | 8/2010 | Goode, Jr. et al. |
| 2010/0217105 A1 | 8/2010 | Yodfat et al. |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228497 A1 | 9/2010 | Kamath et al. |
| 2010/0240975 A1 | 9/2010 | Goode, Jr. et al. |
| 2010/0240976 A1 | 9/2010 | Goode, Jr. et al. |
| 2010/0261987 A1 | 10/2010 | Kamath et al. |
| 2010/0262201 A1 | 10/2010 | He et al. |
| 2010/0274107 A1 | 10/2010 | Boock et al. |
| 2010/0280341 A1 | 11/2010 | Boock et al. |
| 2010/0286496 A1 | 11/2010 | Simpson et al. |
| 2010/0298684 A1 | 11/2010 | Leach et al. |
| 2010/0324392 A1 | 12/2010 | Yee et al. |
| 2010/0324403 A1 | 12/2010 | Brister et al. |
| 2010/0331642 A1 | 12/2010 | Bruce et al. |
| 2010/0331644 A1 | 12/2010 | Neale et al. |
| 2010/0331648 A1 | 12/2010 | Kamath et al. |
| 2010/0331653 A1 | 12/2010 | Stafford |
| 2010/0331656 A1 | 12/2010 | Mensinger et al. |
| 2010/0331657 A1 | 12/2010 | Mensinger et al. |
| 2011/0004085 A1 | 1/2011 | Mensinger et al. |
| 2011/0009727 A1 | 1/2011 | Mensinger et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0040256 A1 | 2/2011 | Bobroff et al. |
| 2011/0040263 A1 | 2/2011 | Hordum et al. |
| 2011/0046467 A1 | 2/2011 | Simpson et al. |
| 2011/0054275 A1 | 3/2011 | Stafford |
| 2011/0060196 A1 | 3/2011 | Stafford |
| 2011/0073475 A1 | 3/2011 | Kastanos et al. |
| 2011/0077490 A1 | 3/2011 | Simpson et al. |
| 2011/0082484 A1 | 4/2011 | Saravia et al. |
| 2011/0106126 A1 | 5/2011 | Love et al. |
| 2011/0118579 A1 | 5/2011 | Goode et al. |
| 2011/0118580 A1 | 5/2011 | Goode et al. |
| 2011/0124992 A1 | 5/2011 | Brauker et al. |
| 2011/0124997 A1 | 5/2011 | Goode et al. |
| 2011/0125410 A1 | 5/2011 | Goode et al. |
| 2011/0130970 A1 | 6/2011 | Goode et al. |
| 2011/0130971 A1 | 6/2011 | Goode et al. |
| 2011/0130998 A1 | 6/2011 | Goode et al. |
| 2011/0137257 A1 | 6/2011 | Gyrn et al. |
| 2011/0144465 A1 | 6/2011 | Shults et al. |
| 2011/0178378 A1 | 7/2011 | Brister et al. |
| 2011/0178461 A1 | 7/2011 | Chong et al. |
| 2011/0184258 A1 | 7/2011 | Stafford |
| 2011/0190603 A1 | 8/2011 | Stafford |
| 2011/0190614 A1 | 8/2011 | Brister et al. |
| 2011/0191044 A1 | 8/2011 | Stafford |
| 2011/0201910 A1 | 8/2011 | Rasdal et al. |
| 2011/0201911 A1 | 8/2011 | Johnson et al. |
| 2011/0218414 A1 | 9/2011 | Kamath et al. |
| 2011/0231107 A1 | 9/2011 | Brauker et al. |
| 2011/0231140 A1 | 9/2011 | Goode, Jr. et al. |
| 2011/0231141 A1 | 9/2011 | Goode, Jr. et al. |
| 2011/0231142 A1 | 9/2011 | Goode, Jr. et al. |
| 2011/0253533 A1 | 10/2011 | Shults et al. |
| 2011/0257895 A1 | 10/2011 | Brauker et al. |
| 2011/0263958 A1 | 10/2011 | Brauker et al. |
| 2011/0270062 A1 | 11/2011 | Goode, Jr. et al. |
| 2011/0270158 A1 | 11/2011 | Brauker et al. |
| 2011/0275919 A1 | 11/2011 | Petisce et al. |
| 2011/0288574 A1 | 11/2011 | Curry et al. |
| 2011/0290645 A1 | 12/2011 | Brister et al. |
| 2011/0313543 A1 | 12/2011 | Brauker et al. |
| 2011/0319729 A1 | 12/2011 | Donnay et al. |
| 2011/0319733 A1 | 12/2011 | Stafford |
| 2011/0319738 A1 | 12/2011 | Woodruff et al. |
| 2011/0319739 A1 | 12/2011 | Kamath et al. |
| 2011/0320130 A1 | 12/2011 | Valdes et al. |
| 2012/0010642 A1 | 1/2012 | Lee et al. |
| 2012/0035445 A1 | 2/2012 | Boock et al. |
| 2012/0040101 A1 | 2/2012 | Tapsak et al. |
| 2012/0046534 A1 | 2/2012 | Simpson et al. |
| 2012/0078071 A1 | 3/2012 | Bohm et al. |
| 2012/0108934 A1 | 5/2012 | Valdes et al. |
| 2012/0108983 A1 | 5/2012 | Banet et al. |
| 2012/0143135 A1 | 6/2012 | Cole et al. |

FOREIGN PATENT DOCUMENTS

| | | |
|---|---|---|
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 1177802 | 2/2002 |
| EP | 0987982 | 1/2007 |
| EP | 2060284 | 5/2009 |
| EP | 2201969 | 6/2010 |
| EP | 2327362 | 6/2011 |
| EP | 2335587 | 6/2011 |
| JP | 11-506629 | 6/1999 |
| JP | 2004-520103 | 7/2004 |
| JP | 2004-520898 | 7/2004 |
| WO | WO-91/15993 | 10/1991 |
| WO | WO-92/13271 | 8/1992 |
| WO | WO-94/20602 | 9/1994 |
| WO | WO-96/39977 | 5/1996 |
| WO | WO-96/25089 | 8/1996 |
| WO | WO-98/35053 | 8/1998 |
| WO | WO-98/56293 | 12/1998 |
| WO | WO-99/33504 | 7/1999 |
| WO | WO-99/56613 | 11/1999 |
| WO | WO-00/49940 | 8/2000 |
| WO | WO-00/59370 | 10/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/50534 | 6/2002 |
| WO | WO-02/058537 | 8/2002 |
| WO | WO-03/028784 | 4/2003 |
| WO | WO-03/076893 | 9/2003 |
| WO | WO-03/082091 | 10/2003 |
| WO | WO-2004/028337 | 4/2004 |
| WO | WO-2004/060436 | 7/2004 |
| WO | WO-2004/061420 | 7/2004 |
| WO | WO-2004/098684 | 11/2004 |
| WO | WO-2004/112602 | 12/2004 |
| WO | WO-2005/084534 | 9/2005 |
| WO | WO-2005/089103 | 9/2005 |
| WO | WO-2006/024671 | 3/2006 |
| WO | WO-2006/042811 | 4/2006 |
| WO | WO-2006/108809 | 10/2006 |
| WO | WO-2007/089738 | 8/2007 |
| WO | WO-2007140783 | 12/2007 |
| WO | WO 2008/065646 | 6/2008 |
| WO | WO 2008/133702 | 11/2008 |
| WO | WO-2009/062675 | 5/2009 |
| WO | WO 2010/112521 | 10/2010 |
| WO | WO-2011002815 | 1/2011 |

OTHER PUBLICATIONS

Bennion, N., et al., "Alternate Site Glucose Testing: A Crossover Design", Diabetes Technology & Therapeutics, vol. 4, No. 1, 2002, pp. 25-33.

Claremont, D. J., et al., "Biosensors for Continuous In Vivo Glucose Monitoring", Proceedings of the Annual International Conference of the IEEE Engineering in Medicine and Biology Society, vol. 10, 1988.

(56) References Cited

OTHER PUBLICATIONS

Clark Jr., L. C., et al., "Electrode Systems for Continuous Monitoring in Cardiovascular Surgery", Annals New York Academy of Sciences, 1962, pp. 29-45.
Clark Jr., L. C., et al., "Long-term Stability of Electroenzymatic Glucose Sensors Implanted in Mice", American Society of Artificial Internal Organs Transactions, vol. XXXIV, 1988, pp. 259-265.
Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240-1244.
Csoregi, E., et al., "Design, Characterization, and One-Point in Vivo Calibration of a Subcutaneously Implanted Glucose Electrode", Analytical Chemistry, vol. 66 No. 19, 1994, pp. 3131-3138.
Feldman, B., et al., "A Continuous Glucose Sensor Based on Wired Enzyme™ Technology—Results from a 3-Day Trial in Patients with Type 1 Diabetes", Diabetes Technology & Therapeutics, vol. 5, No. 5, 2003, pp. 769-779.
Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.
Isermann, R., "Supervision, Fault-Detection and Fault-Diagnosis Methods—An Introduction", Control Engineering Practice, vol. 5, No. 5, 1997, pp. 639-652.
Gunasingham, et al., "Electrochemically Modulated Optrode for Glucose", Biosensors & Bioelectronics, vol. 7, 1992, pp. 353-359.
Ikeda, T., et al., "Artificial Pancreas—Investigation of the Stability of Glucose Sensors Using a Telemetry System" (English language translation of abstract), Jpn. J. Artif. Organs, vol. 19, No. 2, 1990, 889-892.
Isermann, R., et al., "Trends in the Application of Model-Based Fault Detection and Diagnosis of Technical Processes", Control Engineering Practice, vol. 5, No. 5, 1997, pp. 709-719.
Johnson, P. C., "Peripheral Circulation", John Wiley & Sons, 1978, pp. 198.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", Diabetes Care, vol. 24, No. 7, 2001, pp. 1303-1304.
Koudelka, M., et al., "In-Vivo Behaviour of Hypodermically Implanted Microfabricated Glucose Sensors", Biosensors & Bioelectronics, vol. 6, 1991, pp. 31-36.
Lager, W., et al., "Implantable Electrocatalytic Glucose Sensor", Hormone Metabolic Research, vol. 26, 1994, pp. 526-530.
Minimed Technologies, "Tape Tips and Other Infusion Site Information", 1995.
Moatti-Sirat, D., et al., "Evaluating In Vitro and In Vivo the Interference of Ascorbate and Acetaminophen on Glucose Detection by a Needle-Type Glucose Sensor", Biosensors & Bioelectronics, vol. 7, 1992, pp. 345-352.
Moatti-Sirat, D., et al., "Reduction of Acetaminophen Interference in Glucose Sensors by a Composite Nafion Membrane: Demonstration in Rats and Man", Diabetologia, vol. 37, 1994, pp. 610-616.
Olievier, C. N., et al., "In Vivo Measurement of Carbon Dioxide Tension with a Miniature Electrodes", Pflugers Archiv: European Journal of Physiology, vol. 373, 1978, pp. 269-272.
Pickup, J., "Developing Glucose Sensors for In Vivo Use", Tibtech, vol. 11, 1993, pp. 285-291.
Pickup, J., et al., "Implantable Glucose Sensors: Choosing the Appropriate Sensing Strategy", Biosensors, vol. 3, 1987/88, pp. 335-346.
Pickup, J., et al., "Potentially-Implantable, Amperometric Glucose Sensors with Mediated Electron Transfer: Improving the Operating Stability", Biosensors, vol. 4, 1989, pp. 109-119.
Poitout, V., et al., "A Glucose Monitoring System for on Line Estimation in Man of Blood Glucose Concentration Using a Miniaturized Glucose Sensor Implanted in the Subcutaneous Tissue and a Wearable Control Unit", Diabetolgia, vol. 36, 1993, pp. 658-663.
Poitout, V., et al., "Calibration in Dogs of a Subcutaneous Miniaturized Glucose Sensor Using a Glucose Meter for Blood Determination", *Biosensors & Bioelectronics*, vol. 7, 1992, pp. 587-592.
Quinn, C. P., et al., "Kinetics of Glucose Delivery to Subcutaneous Tissue in Rats Measured with 0.3-mm Amperometric Microsensors", The American Physiological Society, 1995, E155-E161.
Roe, J. N., et al., "Bloodless Glucose Measurements", Critical Review in Therapeutic Drug Carrier Systems, vol. 15, Issue 3, 1998, pp. 199-241.
Salehi, C., et al., "A Telemetry-Instrumentation System for Long-Term Implantable Glucose and Oxygen Sensors", Analytical Letters, vol. 29, No. 13, 1996, pp. 2289-2308.
Scheller, F., et al., "Enzyme Electrodes and Their Application", Philosophical Transactions of the Royal Society of London B, vol. 316, 1987, pp. 85-94.
Schmidt, F. J., et al., "Calibration of a Wearable Glucose Sensor", The International Journal of Artificial Organs, vol. 15, No. 1, 1992, pp. 55-61.
Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294-299.
Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401-406.
Shichiri, M., et al., "Membrane Design for Extending the Long-Life of an Implantable Glucose Sensor", Diabetes Nutrition and Metabolism, vol. 2, 1989, pp. 309-313.
Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.
Thompson, M., et al., "In Vivo Probes: Problems and Perspectives", Clinical Biochemistry, vol. 19, 1986, pp. 255-261.
Velho, G., et al., "In Vitro and In Vivo Stability of Electrode Potentials in Needle-Type Glucose Sensors", Diabetes, vol. 38, No. 2, 1989, pp. 164-171.
Von Woedtke, T., et al., "In Situ Calibration of Implanted Electrochemical Glucose Sensors", Biomedica Biochimica Acta, vol. 48, 1989, pp. 943-952.
Chinese Patent Application No. CN 2010800064817, Original Language and English Translation of Office Action mailed Dec. 2, 2014.
European Patent Application No. EP 10739015.5, Extended European Search Report mailed May 10, 2013.
Alcock & Turner, "Continuous analyte monitoring to aid clinical practice," IEEE Engineering in Medicine & BioloXY Magazine, 13:319-25 (1994).
Armour et al., "Application of Chronic Intravascular Blood Glucose Sensor in Dogs," Diabetes, vol. 39, pp. 1519-1526, Dec. 1990.
Bindra, D.S. et al., "Design and in Vitro Studies of a Needle-Type Glucose Sensor for Subcutaneous Monitoring," Anal. Chem., 63(17):1692-1696 (Sep. 1, 1991).
Bobbioni-Harsch, E. et al., "Lifespan of subcutaneous glucose sensors and their performances during dynamic glycaemia changes in rats," J. Biomed. Eng. 15:457-463 (1993).
Cass, A.E.G. et al., "Ferrocene-Mediated Enzyme Electrode for Amperometric Determination of Glucose," Anal. Chem., 56(4):667-671 (Apr. 1984).
Gregg, B. A. et al., "Cross-Linked Redox Gels Containing Glucose Oxidase for Amperometric Biosensor Applications," Analytical Chemistry, 62(3):258-263 (Feb. 1, 1990).
Harrison, DJ. et al., "Characterization of Perfluorosulfonic Acid Polymer Coated Enzyme Electrodes and a Miniaturized Integrated Potentiostat for Glucose Analysis in Whole Blood," Anal. Chem., 60 (19):2002-2007 (Oct. 1, 1988).
Heller, A., "Electrical Connection of Enzyme Redox Centers to Electrodes," J. Phys. Chern., 96 (9):3579-3587 (1992).
Heller, A., "Electrical Wring of Redox Enzymes," Acc. Chem. Res., 23(5):129-134 (1990).
International Search Report and Written Opinion from PCT/US2010/022860 mailed Mar. 23, 2010.

(56) References Cited

OTHER PUBLICATIONS

International Search Report and Written Opinion from PCT/US2010/047381 mailed Oct. 15, 2010.
International Search Report and Written Opinion from PCT/US2010/050772 mailed Dec. 3, 2010.
International Search Report and Written Opinion from PCT/US2010/050888 mailed Nov. 29, 2010.
International Search Report and Written Opinion from PCT/US2010/051861 mailed Nov. 30, 2010.
Johnson, K., et al., "In vivo evaluation of an electroenzymatic glucose sensor implanted in subcutaneous tissue," Biosensors and Bioelectronics. 1992, vol. 7, pp. 709-714.
Maidan, R. et al., "Elimination of Electroaxidizable Interferant-Produced Currents in Amperometric Biosensors," Analytical Chemistry, 64(23):2889-2896 (Dec. 1, 1992).
Mastrototaro, J.J., et al., "An Electroenzymatic Glucose Sensor Fabricated on a Flexible Substrate," Sensors and Biosensors B Chemical, B5: 139-144 (1991).
McKean, B., et al., "A Telemetry-Instrumentation System for Chronically Implanted Glucose and Oxygen Sensors," IEEE Transactions on Biomedical Engineering, vol. 35, No. 7, (Jul. 1988), pp. 526-532.
Moatti-Sirat, D., et al., "Towards continuous glucose monitoring: in vivo evaluation of a miniaturized glucose sensor implanted for several days in rat subcutaneous tissue," Diabetolocia, 35(3) (1 page—Abstract only) (Mar. 1992).
Ohara, T. J., et al., "Glucose Electrodes Based on Cross-Linked $[Os(bpy)_2Cl]^{+/2+}$ Complexed Poly(1-vinylimadazole) Films," Analytical Chemistry, 65(23):3512-3516 (Dec. 1, 1993).
Opinion of the Court, Supreme Court of the United States, No. 04-1350, *KSR International co.*, Petitioner v. *Teleflex Inc. et al.*, Apr. 30, 2007.
Pickup, J. C., et al., "In vivo molecular sensing in diabetes mellitus: an implantable glucose sensor with direct electron transfer," Diabetologia, 32(3):213-217 (1989).
Pishko, M. V., et al., "Amperometric Glucose Microelectrodes Prepared Through Immobilization of Glucose Oxidase in Redox Hydrogels," Anal. Chem., 63(20):2268-2272 (Oct. 15, 1991).
Poitout, V., et al., "In vitro and in vivo evaluation in dogs of a miniaturized glucose sensor," ASAIO Transactions, 37(3) (1 page—Abstract only) (Jul.-Sep. 1991).
Reach, G., et al., "Can Continuous Glucose Monitoring Be Used for the Treatment of Diabetes?," Analytical Chemistry, 64(6):381-386 (Mar. 15, 1992).

Rebrin, K., et al., "Automated Feedback Control of Subcutaneous Glucose Concentration in Diabetic Dogs," Diabetologia, 32(8):573-576 (Aug. 1989).
Sakakida, M., et al., "Ferrocene-mediate needle-type glucose sensor covered with newly designed biocompatible membrane," Sensors and Actuators B, 13-14:319-322 (1993).
Sakakida, M., et al., "Development of ferrocene-mediated needle-type glucose sensor as a measure of true subcutaneous tissue glucose concentrations", Artif Organs Today. 1992, vol. 2, No. 2, pp. 145-458.
Shichiri, M., et al., "Glycaemic Control in Pancrearetomized Dogs with a Wearable Artificial Endocrine Pancreas," Diabetologia, 24(3):179-184 (Mar. 1983).
Shichiri, M., et al., "Telemetry Glucose Monitoring Device with Needle-type Glucose Sensor: A Useful Tool for Blood Glucose Monitoring in Diabetic Individuals," Diabetes Care, vol. 9, No. 3 (May-Jun. 1986), pp. 298-301.
Shichiri, M., et al., "In vivo characteristics of needle-type glucose sensor—Measurement of subcutaneous glucose concentrations in human volunteers," Horm Metab Res Suppl. 1988, vol. 20, pp. 17-20.
Shichiri, M., et al., "Wearable artificial endocrine pancreas with needle-type glucose sensor," The Lancet, 1982, vol. 2, No. 8308, pp. 1129-1131.
Shults, M., "A Telemetry-Instrumentation System for Monitoring Multiple Subcutaneously Implanted Glucose Sensors," IEEE Transactions on Biomedical Engineering, vol. 41, No. 10 (Oct. 1994), pp. 937-942.
Sternberg, R., et al., "Study and Development of Multilayer Needle-type Enzyme-based Glucose Microsensors," Biosensors, 4:27-40 (1988).
Turner, A.P.F., et al., "Diabetes Mellitus: Biosensors for Research and Management", Biosensors, 1:85-115 (1985).
Updike, S. et al., "Principles of Long-term Fully Implanted Sensors with Emphasis on Radiotelemetric Monitoring of Blood Glucase from Inside a Subcataneous Foreign Body Capsule (FBC)" in "Biosensors in the Body: Continuous in vivo Monitoring" (John Wiley & Sons, Ltd., 1997) Chapter 4, pp. 117-137.
Velho, G. et al., "Strategies for calibrating a subcutaneous glucose sensor," Biomed. Biochim. Acta, 48 (11112):957-964 (1989).
Wilson, G. S. et al., "Progress toward the Development of an Implantable Sensor for Glucose," Clinical Chemistry, 38(9):1613-1617 (1992).
Ye, L. et al., "High Current Density "Wired" Quinoprotein Glucose Dehydrogenase Electroade," Anal. Chem., 65(3):238-241 (Feb. 1, 1993).

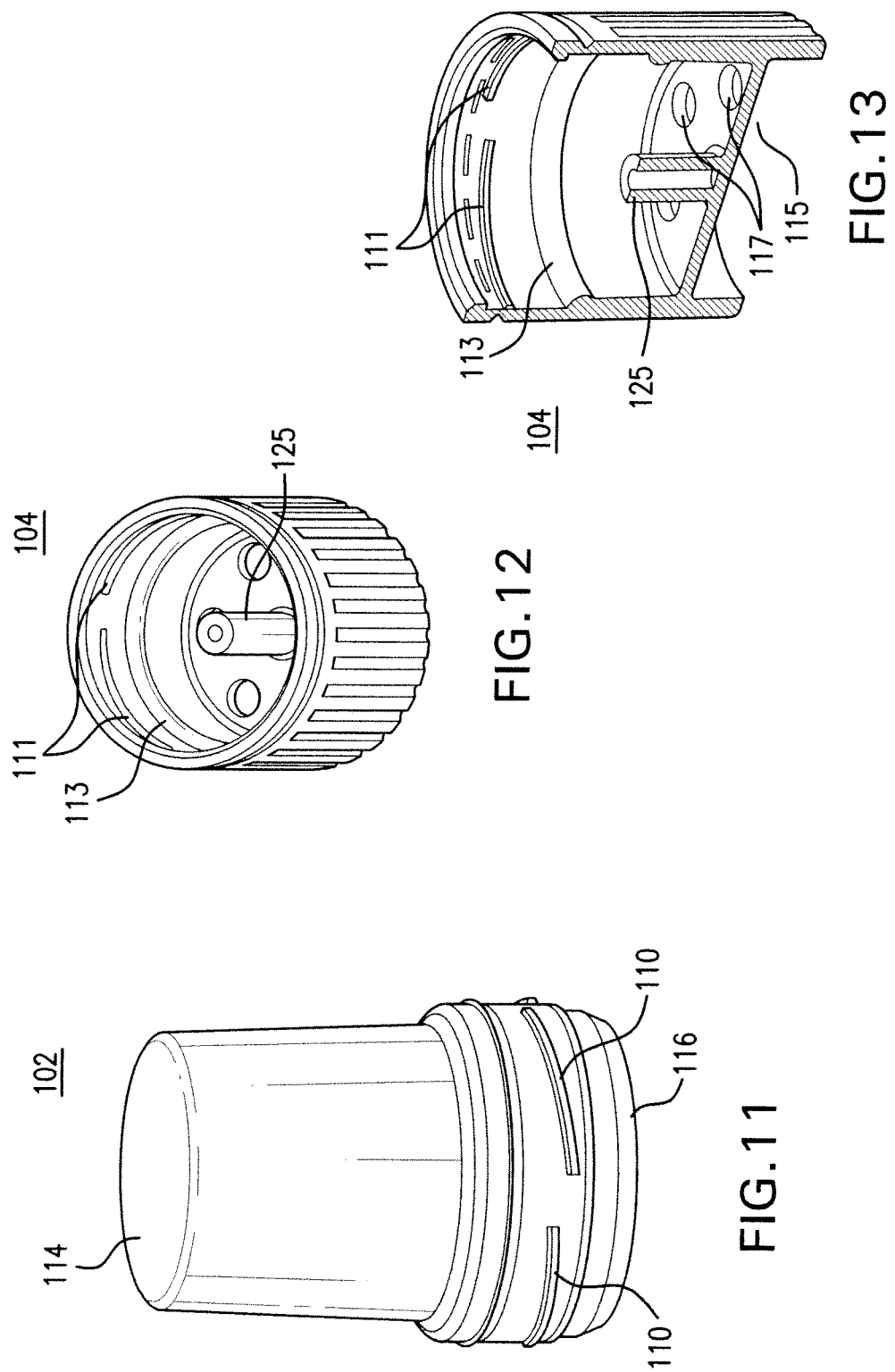

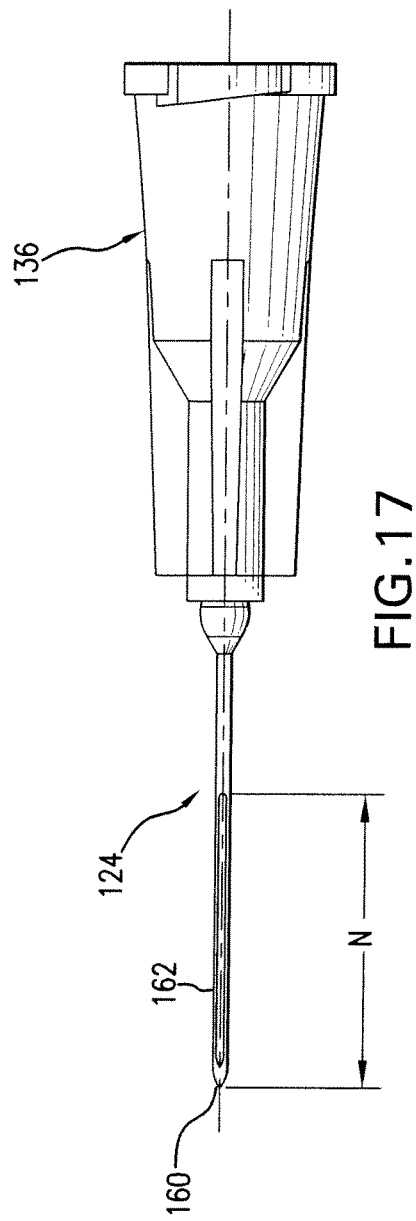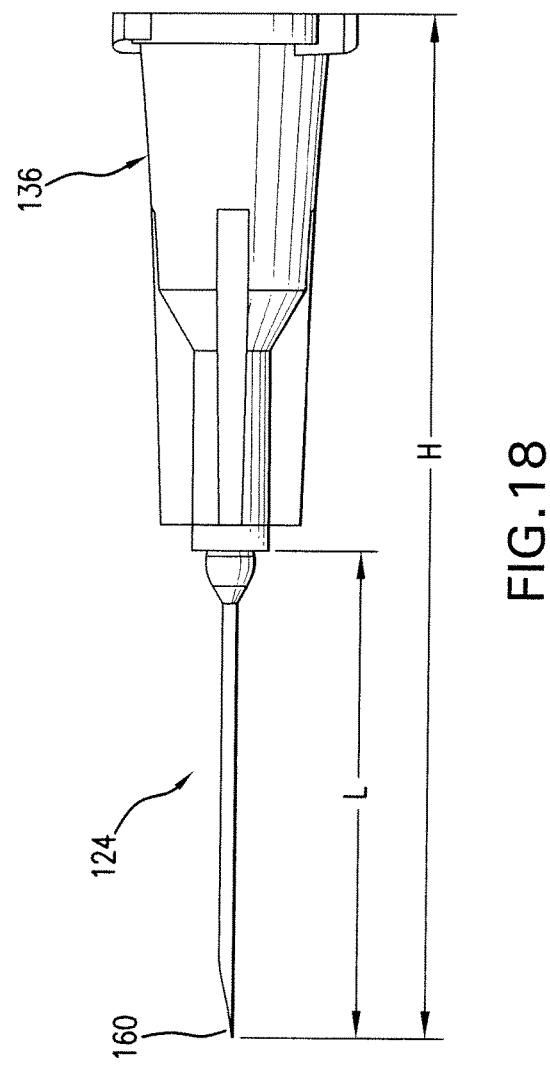

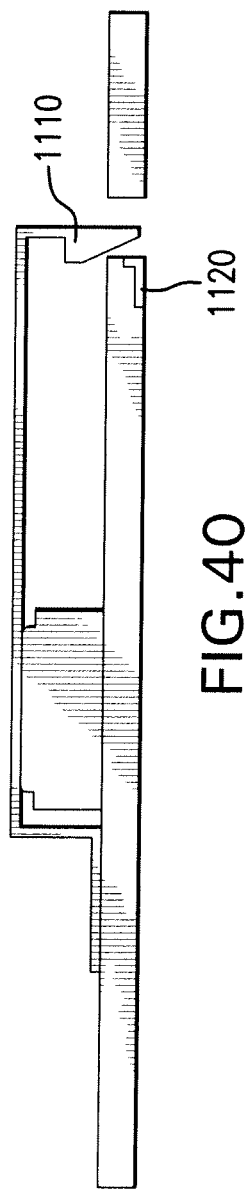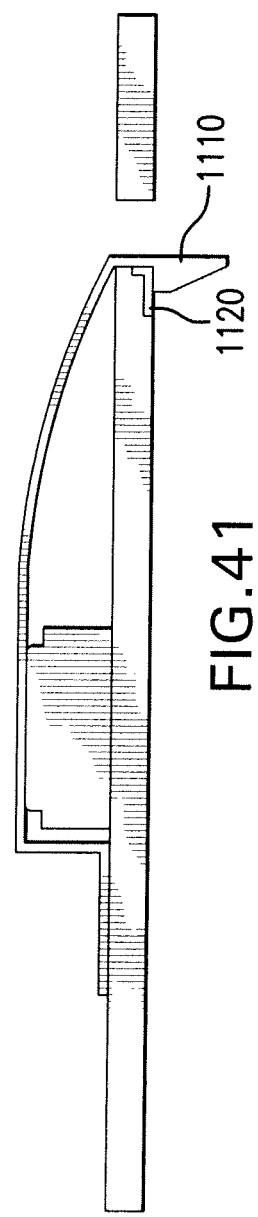

ANALYTE SENSOR AND APPARATUS FOR INSERTION OF THE SENSOR

CROSS-REFERENCE TO RELATED APPLICATIONS

The present application is a continuation of U.S. patent application Ser. No. 12/698,129, filed Feb. 1, 2010, which claims priority to U.S. Provisional Application No. 61/149,639, filed Feb. 3, 2009, both of which are incorporated herein by reference in their entireties for all purposes. This application is further related to U.S. patent application Ser. No. 12/698,124, filed Feb. 1, 2010, the disclosure of which is incorporated by reference in its entirety herein for all purposes.

FIELD OF THE INVENTION

The present invention relates generally to an inserter device, for example, to insert an analyte sensor and/or an infusion set in an animal such as a human.

BACKGROUND OF THE INVENTION

Diabetes Mellitus is an incurable chronic disease in which the body does not produce or properly utilize insulin. Insulin is a hormone produced by the pancreas that regulates blood sugar (glucose). In particular, when blood sugar levels rise, e.g., after a meal, insulin lowers the blood sugar levels by facilitating blood glucose to move from the blood into the body cells. Thus, when the pancreas does not produce sufficient insulin (a condition known as Type 1 Diabetes) or does not properly utilize insulin (a condition known as Type II Diabetes), the blood glucose remains in the blood resulting in hyperglycemia or abnormally high blood sugar levels.

The vast and uncontrolled fluctuations in blood glucose levels in people suffering from diabetes cause long-term, serious complications. Some of these complications include blindness, kidney failure, and nerve damage. Additionally, it is known that diabetes is a factor in accelerating cardiovascular diseases such as atherosclerosis (hardening of the arteries), leading to stroke, coronary heart disease, and other diseases. Accordingly, one important and universal strategy in managing diabetes is to control blood glucose levels.

One way to manage blood glucose levels is testing and monitoring blood glucose levels by using conventional in vitro techniques, such as drawing blood samples, applying the blood to a test strip, and determining the blood glucose level using colorimetric, electrochemical, or photometric test meters. Another more recent technique for monitoring blood glucose levels is by using an in vivo glucose monitoring system, that continuously or automatically tests glucose, such as for example, the FreeStyle Navigator® Continuous Glucose Monitoring System, manufactured by Abbott Diabetes Care Inc. Unlike conventional blood glucose meters, continuous analyte monitoring systems employ an insertable or implantable sensor, which detects and monitors blood glucose levels. Prior to each use of a new sensor, the user self-implants at least a portion of the sensor under his skin. Typically, an inserter assembly is employed to insert the sensor in the body of the user. In this manner, an introducer sharp, while engaged to the sensor, pierces an opening into the skin of the user, releases the sensor and is removed from the body of the user. Accordingly, there exists a need for an easy-to-use, simple, insertion assembly which is reliable, minimizes pain, and is easy to use.

SUMMARY

Sensor assemblies that include a medical device, such as an analyte sensor (e.g., a glucose sensor) and/or an infusion device, and a device to position at least a portion of the medical device beneath a skin surface of a user are provided, as well as methods of positioning at least a portion of a medical device such as an analyte sensor (e.g., a glucose sensor) and/or an infusion device beneath a skin surface of a user, and methods of analyte testing.

Sensor assembly embodiments include a mount adapted to adhere to a skin of a subject; an analyte sensor coupled to the mount, and an insertion sharp having a longitudinal body including a longitudinal opening to receive at least a portion of the sensor body.

In certain embodiments, the sensor includes a body having a proximal section and a distal section, and the distal section may be longitudinally (or otherwise) aligned with the proximal section. Some sensor embodiments may include an intermediate section. An intermediate section, if present, may be laterally displaced from at least the distal member, and a gap may be defined between the laterally displaced intermediate section and a portion of the distal section. In some embodiments, the sensor is integrated with the mount to define an on-body device such as a single unit on-body device. A second gap may be defined in the sensor between the proximal section and the laterally displaced intermediate section. The proximal section of the sensor may have a substantially curved profile.

In some embodiments, the distal section of the sensor body is received in the longitudinally defined opening of the insertion sharp. A gap may be defined between the distal section and the laterally displaced intermediate section, which allows the distal section, in some embodiments a substantial portion—including the entirety of the distal section, to be received in the longitudinal opening of the insertion needle. The intermediate section and the proximal section may be proximate the distal section received in the insertion needle.

In some embodiments, the proximal section of the sensor body is in communication with conductive material disposed on the mount. The conductive material disposed on the mount may define a printed circuit board. The proximal section of the sensor may be disposed in a horizontal plane, and the distal section of the sensor body may be disposed in a vertical plane. In some embodiments, the sensor is a transcutaneous sensor. In some embodiments, the sensor is configured for implantation in a soft tissue of a user. In some embodiments, the sensor is a glucose sensor.

Embodiments include sensor assemblies which include a sensor comprising a portion for operative contact with a fluid of the subject; a mount defining a distal surface adapted for attachment to the skin of a subject and housing a circuit coupled to sensor for performing a function with the sensor; and a switch at least partially disposed in the mount comprising a member having a first position which protrudes from the distal surface of the mount and a second position which is recessed in the mount, the member configured to activate the circuit when in the second position.

In some embodiments, the member is biased in the first position. The member may comprise an elongated member disposed in an opening in the mount. In some embodiments, the member is moved from the first position to the second position when the mount contacts the skin of the subject. In some embodiments, an adhesive layer is disposed on the skin of the subject, and wherein the member is moved from the first position to the second position when the mount contacts the adhesive layer.

In some embodiments, the switch activates the circuit upon the member reaching the second position. In some embodiments, the switch activates the circuit as long as the member is maintained in the second position. In some embodiments, the sensor is a glucose sensor.

In some embodiments, the circuit applies a potential to the sensor. In some embodiments, the circuit applies a current to the sensor.

In some embodiments, a monitor unit is provided to receive information from the sensor/on-body unit. For example, the system is configured for communication (wired or wirelessly) between the on-body unit and a monitor unit, e.g., using radio frequency communication or other protocol. The communication between the two units may be active or passive. In certain embodiments, the on-body unit circuit includes communication components for wired or wireless transmission of signal relating to analyte level monitored by the sensor to the monitor unit. In certain embodiments, RFID components may be included in the on-body unit and monitor unit to enable RFID communication, in which the on-body unit provides data communication to the monitor unit in response to one or more commands or data communication received from the monitor unit. In some embodiments, the transmitter transmits a signal to the receiver automatically, e.g., continuously or in certain embodiments only periodically, such as according to a predetermined schedule. In some embodiments, in addition to or instead of automatic data communication, the on-body unit may transmit signal to the receiver only in response to a request for the data, e.g., received from the monitor unit or otherwise initiated by the user (e.g., activation of a switch on the receiver or on-body unit to initiate data transfer). In some embodiments, a memory is provided, and the circuit stores a signal relating an analyte level provided by the sensor to the memory. In some embodiments, the sensor is a glucose sensor.

Embodiments include apparatuses for inserting medical devices through the skin of a subject. An insertion apparatus may include a sheath defining a distal surface for placement on the skin of the subject; a handle movable between a proximal position and distal position relative to the sheath; a device support for supporting the medical device and defining an aperture therethrough; a sharp support for supporting a sharp extending through said aperture and coupled to the handle; and driver for biasing the handle and the sharp support towards the proximal position.

In some embodiments, the driver comprises a compression member such as a compression spring. In some embodiments, the handle is at least partially disposed within the sheath. In some embodiments, the handle is at least partially disposed surrounding the sheath. In some embodiments, a bellows portion is provided which is disposed between the handle and the sheath.

In some embodiments, the sharp support is permanently fixed to the handle. In some embodiments, the device support is permanently affixed to the handle.

In some embodiments, a stop portion for retaining the device support in the distal position is included. In some embodiments, the device support is coupled to the sharp support until the device support reaches a distal position. In some embodiments, the device support is uncoupled from the sharp support when the device support reaches the distal position. In some embodiments, a retention member is provided to couple the sharp support to the sheath when the sharp support is disposed in the proximal position.

In some embodiments, the medical device is an analyte sensor. In some embodiments, the medical device is a glucose sensor. In some embodiments, the medical device is an infusion set.

In certain embodiments, apparatuses for inserting a medical device through the skin of a subject, are provided which include a sheath defining a distal surface for placement on the skin of the subject; a handle movable between a proximal position and distal position; a device support for supporting the medical device and defining an aperture therethrough, the device support coupled to the handle; a sharp support for supporting a sharp extending through said aperture and coupled to the device support; and driver for biasing the sharp support towards the proximal position.

In some embodiments, the driver comprises a compression spring. In some embodiments, the handle is at least partially disposed surrounding the sheath.

In some embodiments, a stop portion for retaining the device support in the distal position is included. In some embodiments, the device support is coupled to the handle until the device support reaches a distal position. In some embodiments, the device support is uncoupled from the sharp support when the device support reaches the distal position.

Embodiments of analyte sensors are provided which include a body having a proximal section and a distal section. The distal section may be longitudinally aligned with the proximal section. An intermediate section may be included between the proximal and distal sections, and in some embodiments the intermediate section is laterally displaced from at least the distal member. A gap may be defined between the laterally displaced intermediate section and a portion of the distal section.

In some embodiments, the intermediate section is laterally displaced from at least a portion of the proximal section of the sensor body. A second gap may be defined between the laterally displaced intermediate section and the proximal section of the sensor body. The intermediate section may have a distal end and a proximal end, and further the proximal section may be coupled to the proximal section and the distal section may be coupled to the distal section of the sensor body. In some embodiments, the intermediate section is a longitudinal member. The proximal end may be proximate to the gap defined between the distal member and the intermediate member.

In some embodiments, the proximal end is received within a needle seat to create an anchor region to allow the sensor body to slide into an opening defined in the insertion sharp but prevent the sensor body from inadvertently slipping out of the insertion needle. In some embodiments, a width of the distal section of the sensor body is sized to fit within the opening of the insertion sharp having a diameter less than about 22 to about 24 gauge.

In some embodiments, the intermediate member includes a plane-altering portion. The plane-altering portion allows the proximal section of the sensor body to be in a plane different than the distal section of the sensor body. In some embodiments, the proximal section and the distal section are in planes substantially perpendicular to each other, e.g., the area may define an angle of about 120° to about 60°, e.g., about 90 degrees.

In some embodiments, the proximal section has a curved portion.

In some embodiments, the sensor body includes conductive material disposed in or on a surface thereto to define one or more electrodes. The sensor body may include conductive material defining traces disposed in or on a surface of the sensor body. The traces are in communication with the one or more electrodes. The traces may be disposed in or on at least surface of the proximal section of the sensor body. The one or more electrodes may be disposed on the distal section of the sensor body. At least one of the traces or electrodes may include a metal or carbon material such as gold, platinum, titanium, carbon. At least one of the traces or electrodes may be formed by ablation of material. The ablation may include laser ablation.

In some embodiments, the sensor comprises a sensing layer. The sensing layer may comprise an enzyme. The sensing layer may comprise an electron transfer agent. The electron transfer agent may be a redox mediator. In some embodiments, the electron transfer agent includes osmium transition metal complexes and one or more ligands. The electron transfer agent may be configured to transfer electrons directly between the analyte and the working electrode. The electron transfer agent may be configured to transfer electrons indirectly between the analyte and the working electrode.

In some embodiments, the sensing layer comprises a redox polymer. The redox polymer may include osmium. The sensing layer may include a catalyst. The catalyst may include an enzyme. The catalyst may act as an electron transfer agent. In some embodiments, the enzyme includes glucose oxidase. In some embodiments, the enzyme includes glucose dehydrogenase.

In some embodiments, the sensing layer is configured such that the reaction of glucose in the presence of an enzyme forms hydrogen peroxide, and glucose level may be correlated to the level of hydrogen peroxide. In some embodiments, the sensor is a subcutaneous sensor.

These and other features, objects and advantages of the disclosed subject matter will become apparent to those persons skilled in the art upon reading the detailed description as more fully described below.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

FIGS. 11-12 are perspective views of components of the inserter of FIG. 10 in accordance with the disclosed subject matter;

FIG. 13 is a sectional view of a component of the inserter of FIG. 10 in accordance with the disclosed subject matter;

FIGS. 17-18 are schematic views of a needle hub in accordance with one embodiment of the disclosed subject matter;

FIGS. 40-41 illustrate a power supply switch mechanism with a battery contact locking mechanism of the on-body integrated sensor and sensor electronics assembly in accordance with embodiments of the disclosed subject matter;

DETAILED DESCRIPTION OF THE EMBODIMENTS

Figure 1:
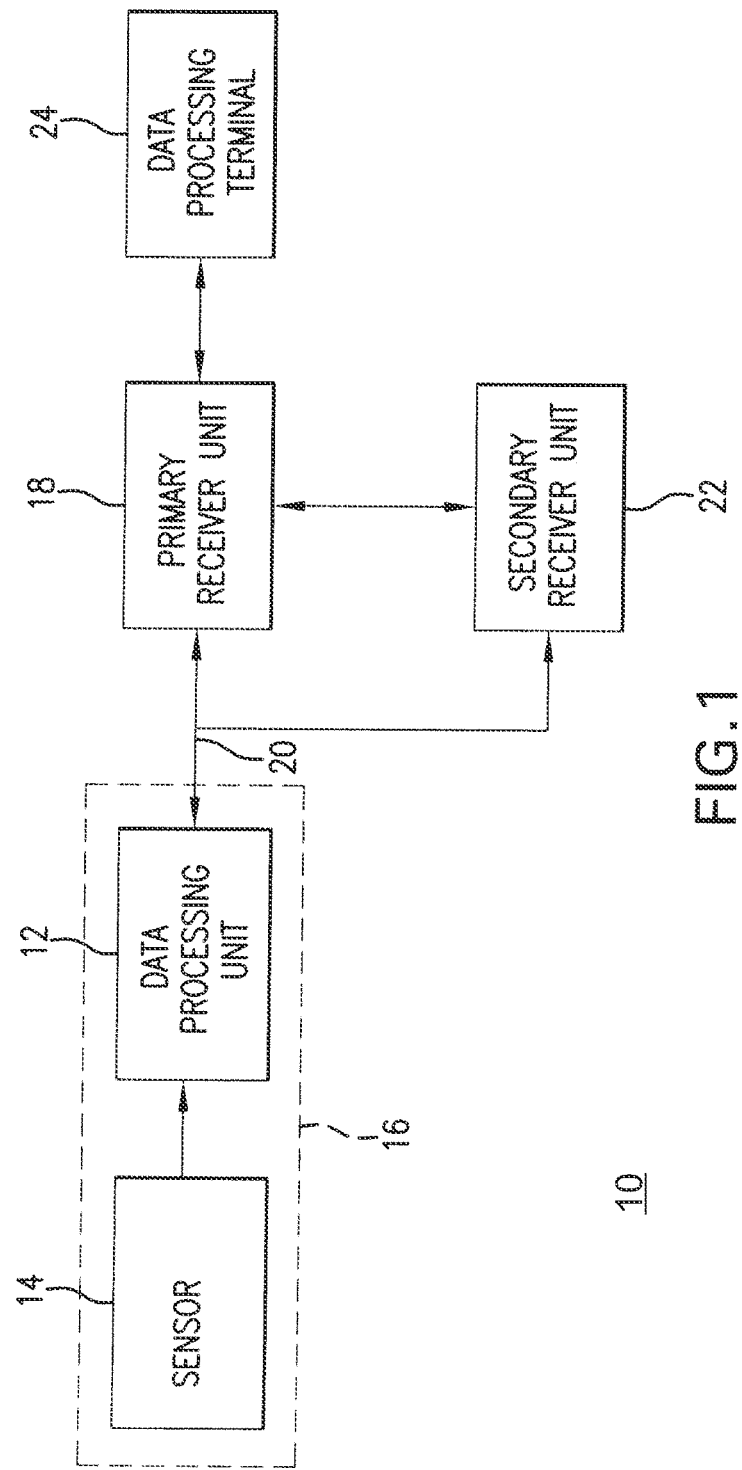
FIG. 1 is a schematic view of the system in accordance with one embodiment of the disclosed subject matter.

A detailed description of the disclosure is provided herein. It should be understood, in connection with the following description, that the subject matter is not limited to particular embodiments described, as the particular embodiments of the subject matter may of course vary. It is also to be understood that the terminology used herein is for the purpose of describing particular embodiments only, and is not intended to be limiting, since the scope of the disclosed subject matter will be limited only by the appended claims.

Where a range of values is provided, it is understood that each intervening value between the upper and lower limit of that range and any other stated or intervening value in that stated range, is encompassed within the disclosed subject matter. Every range stated is also intended to specifically disclose each and every "subrange" of the stated range. That is, each and every range smaller than the outside range specified by the outside upper and outside lower limits given for a range, whose upper and lower limits are within the range from said outside lower limit to said outside upper limit (unless the context clearly dictates otherwise), is also to be understood as encompassed within the disclosed subject matter, subject to any specifically excluded range or limit within the stated range. Where a range is stated by specifying one or both of an upper and lower limit, ranges excluding either or both of those stated limits, or including one or both of them, are also encompassed within the disclosed subject matter, regardless of whether or not words such as "from", "to", "through", or "including" are or are not used in describing the range.

Unless defined otherwise, all technical and scientific terms used herein have the same meaning as commonly understood by one of ordinary skill in the art to which this disclosed subject matter belongs. Although any methods and materials similar or equivalent to those described herein can also be used in the practice or testing of the present disclosed subject matter, this disclosure may specifically mention certain exemplary methods and materials.

All publications mentioned in this disclosure are, unless otherwise specified, incorporated herein by reference for all purposes, including without limitation to disclose and describe the methods and/or materials in connection with which the publications are cited.

The publications discussed herein are provided solely for their disclosure prior to the filing date of the present application. Nothing herein is to be construed as an admission that the present disclosed subject matter is not entitled to antedate such publication by virtue of prior invention. Further, the dates of publication provided may be different from the actual publication dates, which may need to be independently confirmed.

As used herein and in the appended claims, the singular forms "a", "an", and "the" include plural referents unless the context clearly dictates otherwise.

Nothing contained in the Abstract or the Summary should be understood as limiting the scope of the disclosure. The Abstract and the Summary are provided for bibliographic and convenience purposes and due to their formats and purposes should not be considered comprehensive.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosed subject matter. Any recited method can be carried out in the order of events recited, or in any other order which is logically possible. Reference to a singular item, includes the possibility that there are plural of the same item present. When two or more items (for example, elements or processes) are referenced by an alternative "or", this indicates that either could be present separately or any combination of them could be present together except where the presence of one necessarily excludes the other or others.

System Overview

Certain classes of analyte monitors are provided in small, lightweight, battery-powered and electronically-controlled systems. Such a system may be configured to detect signals indicative of in vivo analyte levels using an electrochemical sensor, and collect such signals, with or without processing the signal. In some embodiments, the portion of the system that performs this initial processing may be configured to provide the raw or initially processed data to another unit for further collection and/or processing. Such provision of data may be effected, for example, via a wired connection, such as an electrical, or via a wireless connection, such as an IR or RF connection.

Certain analyte monitoring systems for in vivo measurement employ a sensor that measures analyte levels in interstitial fluids under the surface of the subject's skin. These may be inserted partially through the skin ("transcutaneous") or entirely under the skin ("subcutaneous"). A sensor in such a system may operate as an electrochemical cell. Such a sensor may use any of a variety of electrode configurations, such as a three-electrode configuration (e.g., with "working", "reference" and "counter" electrodes), driven by a controlled potential (potentiostat) analog circuit, a two-electrode system configuration (e.g., with only working and counter electrodes), which may be self-biasing and/or self-powered, and/or other configurations. In some embodiments, the sensor may be positioned within a blood vessel.

In certain systems, the analyte sensor is in communication with a sensor control unit. As used in this disclosure, an on-body unit sometimes refers to such a combination of an analyte sensor with such a sensor control unit.

Certain embodiments are modular. The on-body unit may be separately provided as a physically distinct assembly, and configured to provide the analyte levels detected by the sensor over a communication link to a monitor unit, referred to in this disclosure as a "receiver unit" or "receiver device", or in some contexts, depending on the usage, as a "display unit," "handheld unit," or "meter". The monitor unit, in some embodiments, may include, e.g., a mobile telephone device, a personal digital assistant, other consumer electronic device such as MP3 device, camera, radio, etc., or other communication-enabled data processing device.

The monitor unit may perform data processing and/or analysis, etc. on the received analyte data to generate information pertaining to the monitored analyte levels. The monitor unit may incorporate a display screen, which can be used, for example, to display measured analyte levels, and/or audio component such as a speaker to audibly provide information to a user, and/or a vibration device to provide tactile feedback to a user. It is also useful for a user of an analyte monitor to be able to see trend indications (including the magnitude and direction of any ongoing trend), and such data may be displayed as well, either numerically, or by a visual indicator, such as an arrow that may vary in visual attributes, such as size, shape, color, animation, or direction. The receiver device may further incorporate an in vitro analyte test strip port and related electronics in order to be able to make discrete (e.g., blood glucose) measurements.

The modularity of these systems may vary. In some embodiments the sensor is attachable and detachable from the sensor control unit (and the on-body unit may be reusable), while in other embodiments, the sensor and sensor control unit may be provided as an integrated, un-detachable package, which may be disposable after use.

FIG. 1 shows one embodiment of an analyte measurement system 10. In such a system, a data processing unit or sensor control unit 12 may interact with an analyte sensor 14 to obtain signals representative of analyte levels. Sensor control unit 12 may further include communications circuit with associated electronics (not shown). In some embodiments, the sensor control unit 12 and sensor are constructed to be maintained "on the body" of the subject for a period of time that may include hours, days, weeks, or a month or more. Accordingly, the sensor control unit 12 and sensor 14 may be referred to collectively herein as an on-body unit 16. A receiver unit or monitor unit 18 may also be provided. In the embodiment shown, sensor control unit 12 and monitor unit 18 communicate via connection 20 (in this embodiment, a wireless RF connection). Communication may occur, e.g., via RF communication, infrared communication, Bluetooth® communication, Zigbee® communication, 802.1x communication, or WiFi communication, etc. In some embodiments, the communication may include an RF frequency of 433 MHz, 13.56 MHz, or the like. In some embodiments, a secondary monitor unit 22 may be provided. A data processing terminal 24 is useful for providing further processing or review of analyte data.

In certain embodiments, system 10 may be a continuous analyte monitor (e.g., a continuous glucose monitoring system or CGM), and accordingly operate in a mode in which the communications via connection 20 has sufficient range to support a flow of data from on-body unit 16 to monitor unit 18. In some embodiments, the data flow in a CGM system is automatically provided by the on-body unit 16 to the monitor unit 18. For example, no user intervention may be required for the on-body unit 16 to send the data to the monitor unit 18. In some embodiments, the on-body unit 16 provides the signal relating to analyte level to the receiving unit 18 on a periodic basis. For example, the signal may be provided, e.g., automatically sent, on a fixed schedule, e.g., once every 250 ms, once a second, once a minute, etc. In some embodiments, the signal is provided to the monitor unit 18 upon the occurrence of an event, e.g., a hyperglycemic event or a hypoglycemic event, etc. In some embodiments, data processing unit 12 may further include local memory in which it may record, "logged data" or buffered data collected over a period of time and provide the some or all of the accumulated data to monitor unit 18 from time-to-time. Or, a separate data logging unit may be provided to acquire periodically transmitted data from a transmitter device. Data transmission in a CGM system may be one-way communication, e.g., the on-body unit 16 provides data to the monitor unit 18 without receiving signals from the monitor unit 18. In some embodiments, two-way communication is provided between the on-body unit 16 and the monitor unit 18.

In some embodiments, a signal is provided to the monitor unit 18 "on demand." According to such embodiments, the monitor unit 18 requests a signal from the on-body unit 16, or the on-body unit 16 may be activated to send signal upon activation to do so. Accordingly, one or both of the on-body unit 16 and monitor unit 18 may include a switch activatable by a user or activated upon some other action or event, the activation of which causes analyte-related signal to be transferred from the on-body unit 16 to the monitor unit 18. For example, the monitor unit 18 is placed in close proximity with a transmitter device and initiates a data transfer, either over a wired connection, or wirelessly by various means, including, for example various RF-carried encodings and protocols and IR links.

In some embodiments, the signal relating to analyte level is instantaneously generated by the analyte sensor 14 upon receipt of the request, and transmitted to the monitor unit 18 as requested, and/or the signal relating to analyte level is periodically obtained, e.g., once every 250 ms, once a second, once a minute, etc. Upon receipt of the "on demand" request at the on-body unit 16, an analyte signal is provided to the monitor unit. In some cases, the signal provided to the monitor unit 18 is or at least includes the most recent analyte signal(s).

In further embodiments, additional data is provided to the monitor unit 18 "on demand." For example, analyte trend data may be provided. Such trend data may include two or more analyte data points to indicate that analyte levels are rising, falling, or stable. Analyte trend data may include data from longer periods of time, such as, e.g., several minutes, several hours, several days, or several weeks.

Further details regarding on demand systems are disclosed in U.S. Pat. No. 7,620,438, U.S. Patent Publication Nos. 2009/0054749 A1, published Feb. 26, 2009; 2007/0149873 A1, published Jun. 28, 2007, now U.S. Pat. No. 9,014,773; 2008/0064937 A1, published Mar. 13, 2008; 2008/0071157 A1, published Mar. 20, 2008; 2008/0071158 A1, published Mar. 20, 2008; 2009/0281406 A1, published Nov. 12, 2009; 2008/0058625 A1, published Mar. 6, 2008, now U.S. Pat. No. 7,920,907; 2009/0294277 A1, published Dec. 3, 2009; 2008/0319295 A1, published Dec. 25, 2008, now U.S. Pat. No. 8,597,188; 2008/0319296 A1, published Dec. 25, 2008, now U.S. Pat. No. 8,617,069; 2009/0257911 A1, published Oct. 15, 2009, now U.S. Pat. No. 8,252,229; 2008/0179187 A1, published Jul. 31, 2008, now U.S. Pat. No. 8,808,515, 2007/0149875 A1, published Jun. 28, 2007, now U.S. Pat. No. 8,515,518; 2009/0018425 A1, published Jan. 15, 2009, now U.S. Pat. No. 8,160,670; and U.S. patent application Ser. No. 12/625,524, filed Nov. 24, 2009, now U.S. Pat. No. 8,390,455; Ser. No. 12/625,525, filed Nov. 24, 2009, now U.S. Pat. No. 8,358,210; Ser. No. 12/625,528, filed Nov. 24, 2009, now U.S. Pat. No. 8,115,635; Ser. No. 12/628,201, filed Nov. 30, 2009, now U.S. Patent Publication No. 2010/0076280; Ser. No. 12/628,177, filed Nov. 30, 2009, now U.S. Patent Publication No. 2010/0076289; Ser. No. 12/628,198, filed Nov. 30, 2009, now U.S. Patent Publication No. 2010/0076291; Ser. No. 12/628,203, filed Nov. 30, 2009, now U.S. Patent Publication No. 2010/0076292; Ser. No. 12/628,210, filed Nov. 30, 2009, now U.S. Patent Publication No. 2010/0076293; Ser. No. 12/393,921, filed Feb. 26, 2009, now U.S. Patent Publication No. 2010/0213057; 61/149,639, filed Feb. 3, 2009; Ser. No. 12/495,709, filed Jun. 30, 2009, now U.S. Patent Publication No. 2010/0326842; 61/155,889, filed Feb. 26, 2009; 61/155,891, filed Feb. 26, 2009; 61/155,893, filed Feb. 26, 2009; 61/165,499, filed Mar. 31, 2009; 61/227,967, filed Jul. 23, 2009; 61/163,006, filed Mar. 23, 2009; Ser. No. 12/495,730, filed Jun. 30, 2009, now U.S. Patent Publication No. 2010/0331643; Ser. No. 12/495,712, filed Jun. 30, 2009, now U.S. Pat. No. 8,437,827; 61/238,461, filed Aug. 31, 2009; 61/256,925, filed Oct. 30, 2009; 61/238,494, filed Aug. 31, 2009; 61/238,159, filed Aug. 29, 2009; 61/238,483, filed Aug. 31, 2009; 61/238,581, filed Aug. 31, 2009; 61/247,508, filed Sep. 30, 2009; 61/247,516, filed Sep. 30, 2009; 61/247,514, filed Sep. 30, 2009; 61/247,519, filed Sep. 30, 2009; 61/249,535, filed Oct. 7, 2009; Ser. No. 12/544,061, filed Aug. 19, 2009, now U.S. Patent Publication No. 2011/0046466; Ser. No. 12/625,185, filed Nov. 24, 2009, now U.S. Pat. No. 8,354,013; Ser. No. 12/625,208, filed Nov. 24, 2009, now U.S. Pat. No. 9,042,954; Ser. No. 12/624,767, filed Nov. 24, 2009, now U.S. Patent Publication No. 2011/0124993; Ser. No. 12/242,780, filed Sep. 30, 2008, now U.S. Pat. No. 8,983,568; Ser. No. 12/183,602, filed Jul. 31, 2008, now U.S. Patent Publication No. 2010/0030052; Ser. No. 12/211,014, filed Sep. 15, 2008, now U.S. Pat. No. 8,636,884; and Ser. No. 12/114,359, filed May 2, 2008, now U.S. Pat. No. 8,080,385, each of which is incorporated by reference in its entirety herein.

The Sensor

The analyte sensor 14 of the analyte measurement system 10 may be used to monitor levels of a wide variety of analytes. Analytes that may be monitored include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. One or more analyte may be monitored by a given sensor.

In one embodiment of the present disclosure, sensor 14 is physically positioned in or on the body of a user whose analyte level is being monitored. Sensor 14 may be configured to continuously sample the analyte level of the user and convert the sampled analyte level, e.g., glucose concentration into a corresponding data signal, e.g., a current or voltage, for input into sensor control unit electronics. Alternatively, sensor 14 may be configured to sample analyte levels on demand. The sensor control unit electronics may amplify, filter, or otherwise process the signal provided by the sensor.

The sensor may take on a number of forms. For example, the sensor may include a flexible or rigid substrate. In some embodiments, the sensor may be a wire. In some embodiments, the sensor may include two or three or more electrodes.

Figure 2:
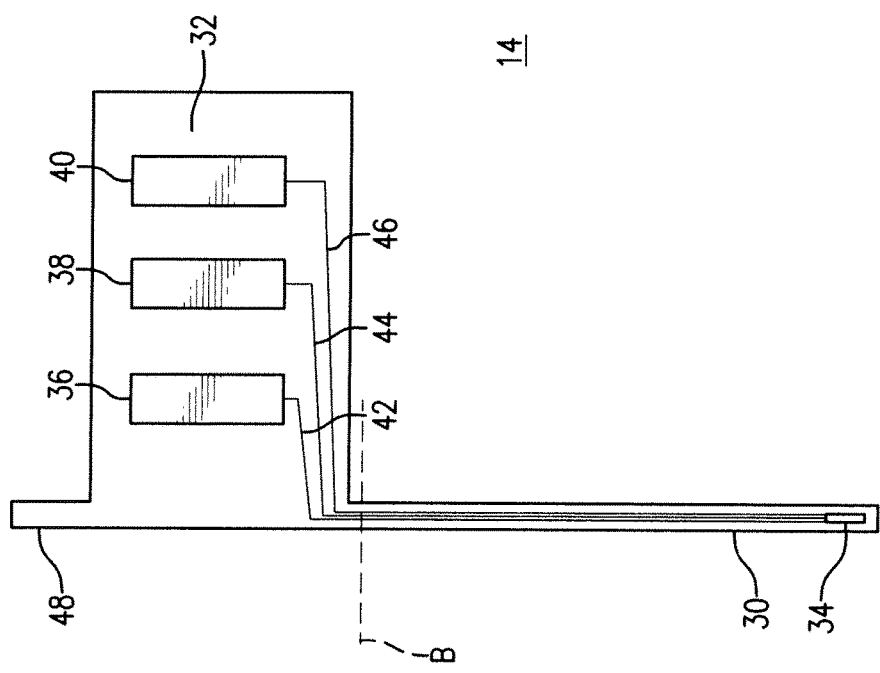
FIG. 2 is a view, in partial cross section, of an electrochemical sensor in accordance with one embodiment of the disclosed subject matter.

An embodiment of the sensor 14 is illustrated in FIG. 2. In some embodiments, sensor 14 includes a substrate which is a dielectric, e.g., a polymer or plastic material, such as polyester or polyamide. In this embodiment, the sensor is constructed so that a portion is positionable beneath skin and a portion is above skin. Accordingly, sensor 14 includes an insertion portion 30 and a contact portion 32. The contact portion 32 typically includes several conductive contacts 36, 38, and 40 (herein shown as 3 contacts) for connection to other electronics, e.g., at the data processing unit 12. The contacts provided in this embodiment are for a working electrode 36, a reference electrode 38, and a counter electrode 40. In some embodiments, two or more working electrodes are provided. The operative portions of these electrodes, that is, working electrode, reference electrode, and counter electrode (not individually shown), are provided at the distal end of insertion portion 30. The contact and operative portions of the electrodes are connected by circuit traces 42, 44, and 46 running on the surface of substrate. In some embodiments, the traces are provided in channels, or may be embedded within the substrate, or may traverse different sides of the substrate. The conductive contacts, conductive traces, and electrodes are fabricated from a conductive material, such as platinum, palladium, gold, or conductive carbon. Further details of sensors are described, e.g., in U.S. Pat. Nos. 6,175,572; 6,103,033, which are incorporated by reference herein.

Sensor 14 may include a proximal retention portion 48. In some embodiments, the insertion portion 30 and the proximal retention portion 48 are substantially longitudinally aligned. The insertion portion 30 and the proximal retention portion 48 are sized and configured to be positioned with a sharp for installation into the skin of a subject, as described herein. In use, the sensor 14 may be configured to bend (e.g., along the line B) and therefore be positioned in two substantially perpendicular, intersecting planes.

Figure 3:
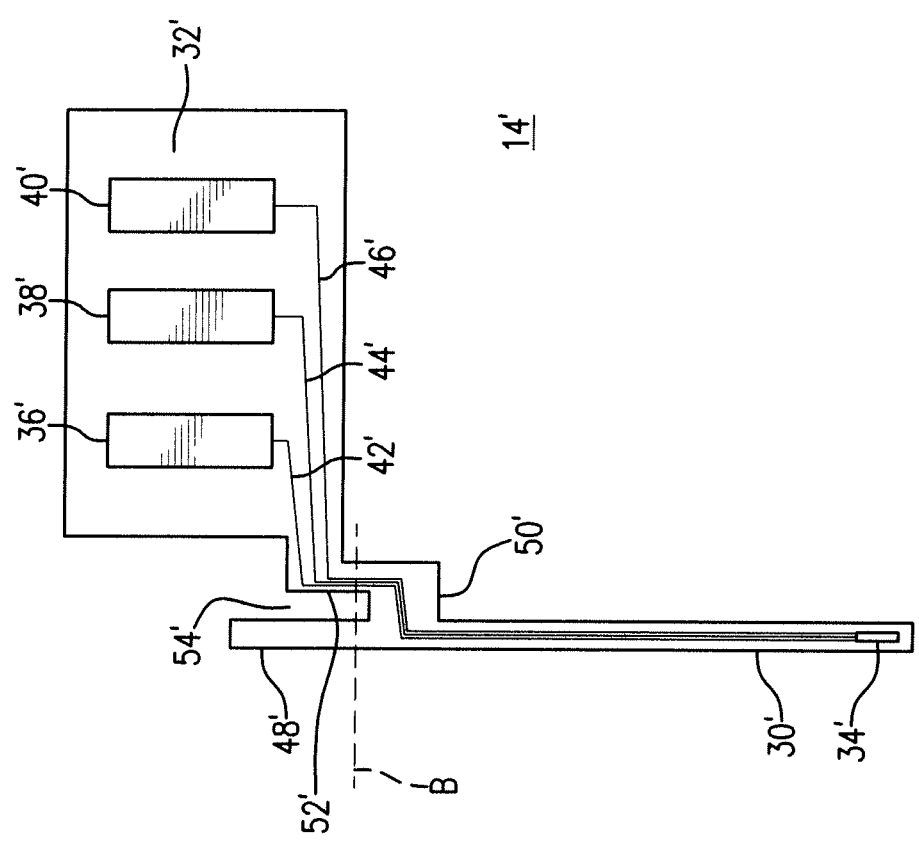
FIG. 3 is a view of an electrochemical sensor in accordance with another embodiment of the disclosed subject matter.
Figure 4:
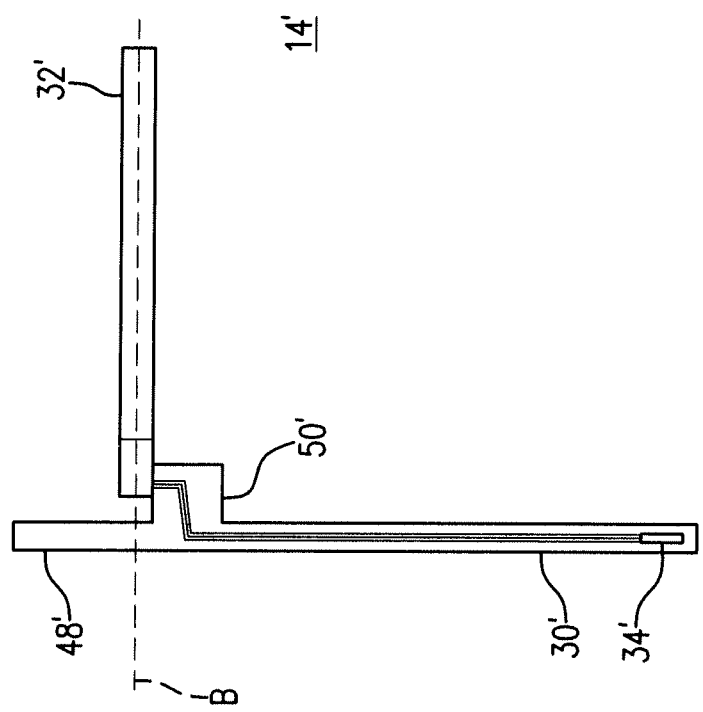
FIG. 4 is a view of the electrochemical sensor of FIG. 3 in a folded configuration in accordance with the disclosed subject matter.

As illustrated in FIG. 3, sensor 14' is substantially identical to sensor 14, with many of the differences illustrated in FIG. 3 and noted herein. Sensor 14' further includes additional features useful for connecting to, e.g., mounting to or in or on, a housing associated with the sensor control unit 12. For example, sensor 14' includes a laterally displaced portion (or sensor tab) 50' and a longitudinal displaced portion 52' which provide a path for electrical connections, e.g., the conductive traces. Sensor 14' is further provided with a notch 54' between the proximal retention portion 48' and the longitudinal displaced portion 52'. Such configuration permits the sensor 14' to bend (e.g., along the line are indicated by line B) and therefore be positioned in two substantially perpendicular, intersecting planes, as illustrated in FIG. 4. As will be described below, the sensor tab 50' can be encased in a portion of the body of the data processing unit 12 to aid in securing and positioning the sensor 14'. Proximal retention portion 48' maintains its longitudinal alignment with insertion portion 30 for positioning within an insertion sharp.

Figure 5:
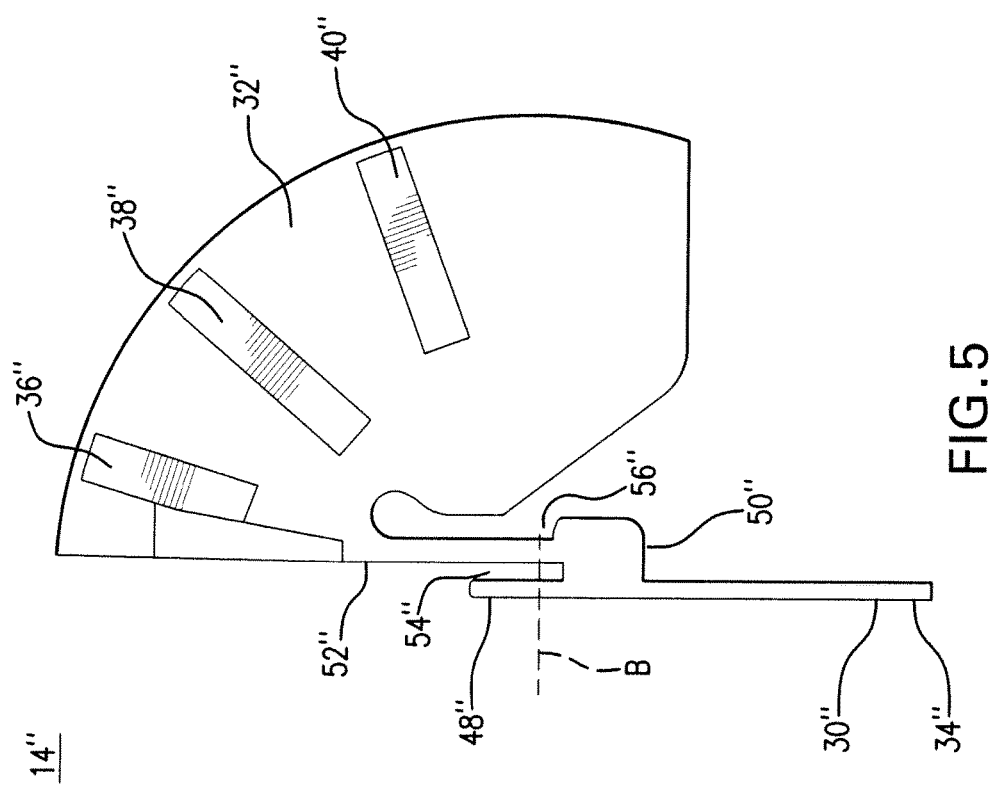
FIG. 5 is a view of an electrochemical sensor in accordance with a further embodiment of the disclosed subject matter.
Figure 6:
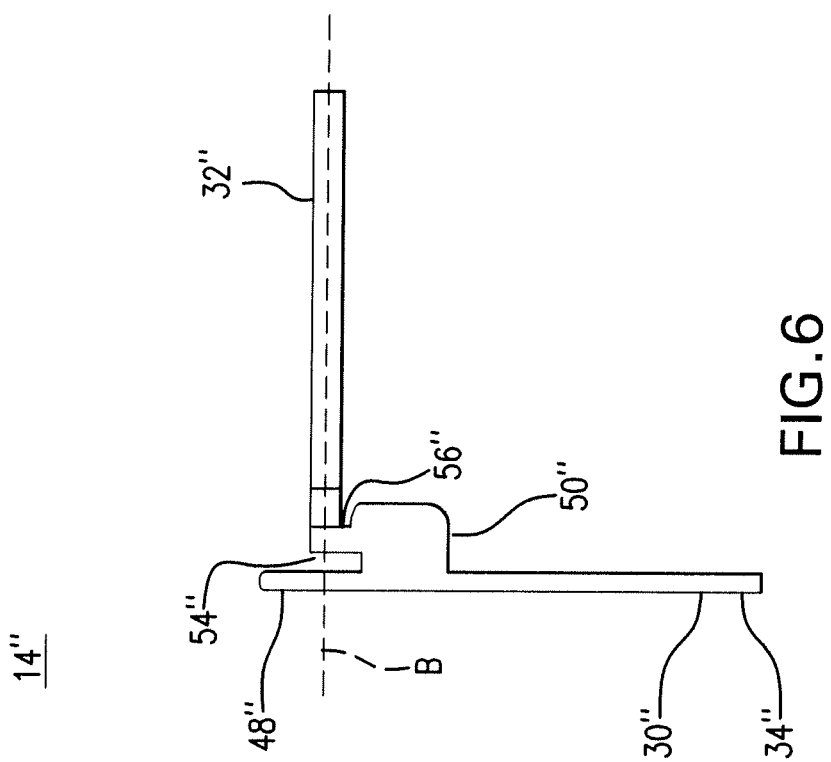
FIG. 6 is a view of the electrochemical sensor of FIG. 5 in a folded configuration in accordance with the disclosed subject matter.

FIG. 5 illustrates a further embodiment of a sensor 14" in accordance with the disclosure. Sensor 14" is substantially identical to sensor 14 and 14', with certain exemplary differences illustrated in FIG. 5 and noted herein. For example, sensor 14" includes a contact portion 32" which defines a fan-like configuration having a curved edge. Sensor 14" defines a sensor flag indentation 56" which also serves to assist in retaining the sensor 14" in vertical direction, as will be described below, and provides a discrete location for mating with a feature of the data processing unit 12, e.g., the bottom surface of a printed circuit board. Sensor 14" is likewise capable of bending along axis B, as illustrated in FIG. 6. In any of the embodiments of the sensor described herein, the distance between insertion portion 30 to retention portion 48 may be, e.g., about 5 mm, or about 10 mm, or about 15 mm, or about 20 mm.

In general, sensors in accordance with the present disclosure operate electrochemically, through an arrangement of electrodes having chemical sensing layers applied thereto, by generating an electrical current proportional to the volume of a redox reaction of the analyte (and indicative of analyte concentration), catalyzed by an analyte-specific oxidizing enzyme. Embodiments exist in which the number of electrodes provided to bring about and detect the level of these reactions is two, three or a greater number.

A portion of sensor 14 (which collectively refers to sensors 14' and 14" herein) may be situated above the surface of the skin, with a distal portion 30 penetrating through the skin and into the subcutaneous space in contact with the user's biofluid, such as interstitial fluid. The disposition of the sensor in the illustrated embodiment is referred to as "transcutaneous". In general, the term "transcutaneous" as used herein refers to a sensor that is only partially inserted under one or more layers of the skin of the user, whereas the term "subcutaneous" refers to a sensor that is completely inserted under one or more layers of the skin of the user. It is understood that many features described herein would be applicable to both transcutaneous and subcutaneous sensors. Further details regarding the electro-chemistry of sensor 14 is provided in U.S. Pat. Nos. 5,264,104; 5,356,786; 5,262,035, 5,320,725, 6,990,366, each of which is incorporated herein by reference In some embodiments, the sensor is implantable into a subject's body for a period of time (e.g., three to seven days, or in some embodiments, longer periods of up to several weeks) to contact and monitor an analyte present in a biological fluid. In this regard, the sensor can be disposed in a subject at a variety of sites (e.g., abdomen, upper arm, thigh, etc.), including intramuscularly, transcutaneously, intravascularly, or in a body cavity. In one embodiment, the sensor can be a transcutaneous glucose sensor. Alternatively, the sensor can be a subcutaneous glucose sensor.

In some embodiments, sensor 14 is employed by insertion and/or implantation into a user's body for some usage period. In such embodiments, substrate may be formed from a relatively flexible material to improve comfort for the user and reduce damage to the surrounding tissue of the insertion site, e.g., by reducing relative movement of the sensor with respect to the surrounding tissue.

While the embodiments illustrated in FIGS. 2-6 have three electrodes, other embodiments can include a fewer or greater number of electrodes. For example, a two electrode sensor can be utilized. The sensor may be externally-powered and allow a current to pass proportional to the amount of analyte present. Alternatively, the sensor itself may act as a current source in some embodiments. In some two-electrode embodiments, the sensor may be self-biasing and there may be no need for a reference electrode. An exemplary self-powered, two-electrode sensor is described in U.S. patent application Ser. No. 12/393,921, filed Feb. 26, 2009, and entitled "Self-Powered Analyte Sensor," which is hereby incorporated by reference in its entirety herein for all purposes. The level of current provided by a self-powered sensor may be low, for example, on the order of nanoamperes.

On-Body Unit

Figure 7:
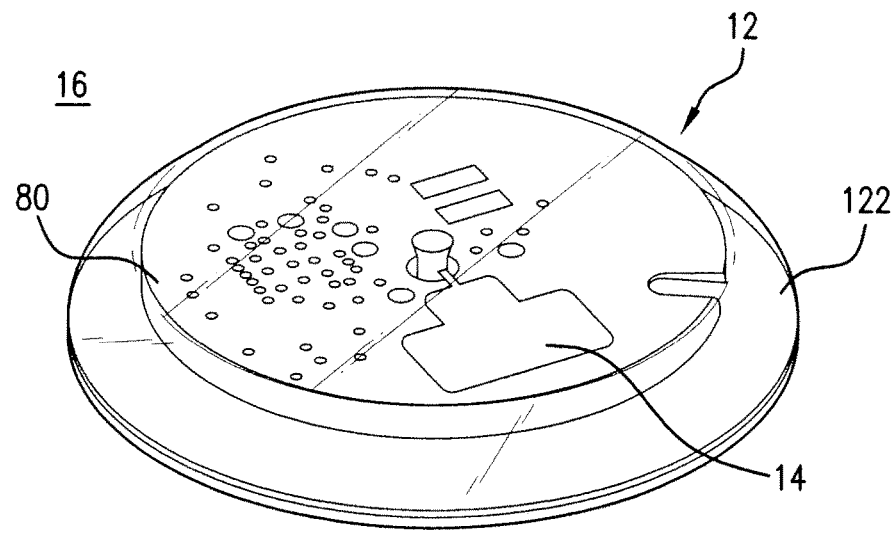
FIG. 7 is a perspective view of an on-body unit in accordance with one embodiment of the disclosed subject matter.
Figure 8:
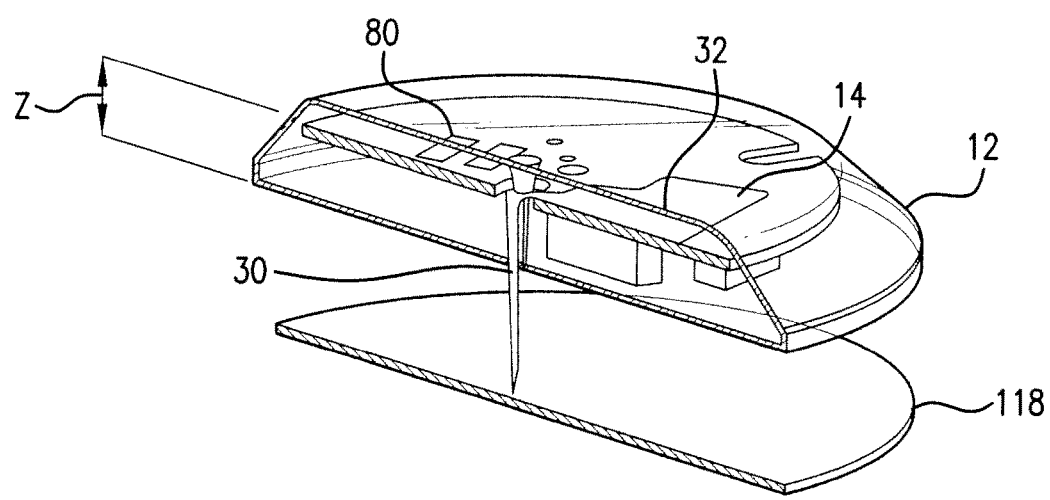
FIG. 8 is a perspective view in partial cross-section of an on-body unit of FIG. 7 in accordance with the disclosed subject matter.

An exemplary configuration for sensor 14 (and sensors 14' and 14") and sensor control unit 12 (e.g., collectively on-body unit 16) is illustrated in FIGS. 7-8. Data processing unit 12, may be provided with a substantially circular configuration having a reduced height (i.e., "Z"-dimension) to provide a low-profile when sitting on the skin of the subject. In some embodiments, the height is about 3 mm to about 25 mm, e.g., may be about 4 mm, about 5 mm, about 10 mm, or about 15 mm. In certain embodiments, the unit 12 may have a variable height. Data processing unit 12, including its associated electronics 80, are housing in a sensor housing 122. For example, electronics may include, e.g., an analog interface for connecting to the sensor 14, a processor, and a power supply. A serial communication section may be provided. A temperature sensor, such as a thermistor, which detects skin and or ambient temperature may be included to provide compensation to the analyte signal. A RF communication circuit is provided to communicate with the monitor unit 18. A data storage unit may be provided to store analyte data points over a short term, e.g., several hours or minutes, or over a long term, e.g., several days or weeks. Additional optional electronics include a serial communication section, a leakage detection circuit, or user input, e.g., a switch to activate/deactivate some or all of the device. Many of the components may be combined together and/or their function provided by common components. Furthermore, certain components may be eliminated entirely. For example, a power supply may be omitted if power is provided by inductive coupling.

In some embodiments, sensor 14 is disposed within the data transmitting unit 12, e.g., in a bent configuration, as illustrated in certain embodiments herein, e.g., in FIGS. 4 and 6. The contact portion 32 of sensor 14 may be oriented in a substantially horizontal configuration, and secured to a printed circuit board of the transmitter unit 12. The insertion portion 30 of the sensor 14 extends in a substantially downwardly vertical orientation for placement in the skin of the subject. It is understood that sensor 14 may be disposed in other configurations, e.g., in an entirely substantially vertical configuration, etc. As a further example, the insertion portion 30 may be disposed at an oblique angle, e.g., between about 0° and about 90° with respect to the skin surface.

Figure 9:
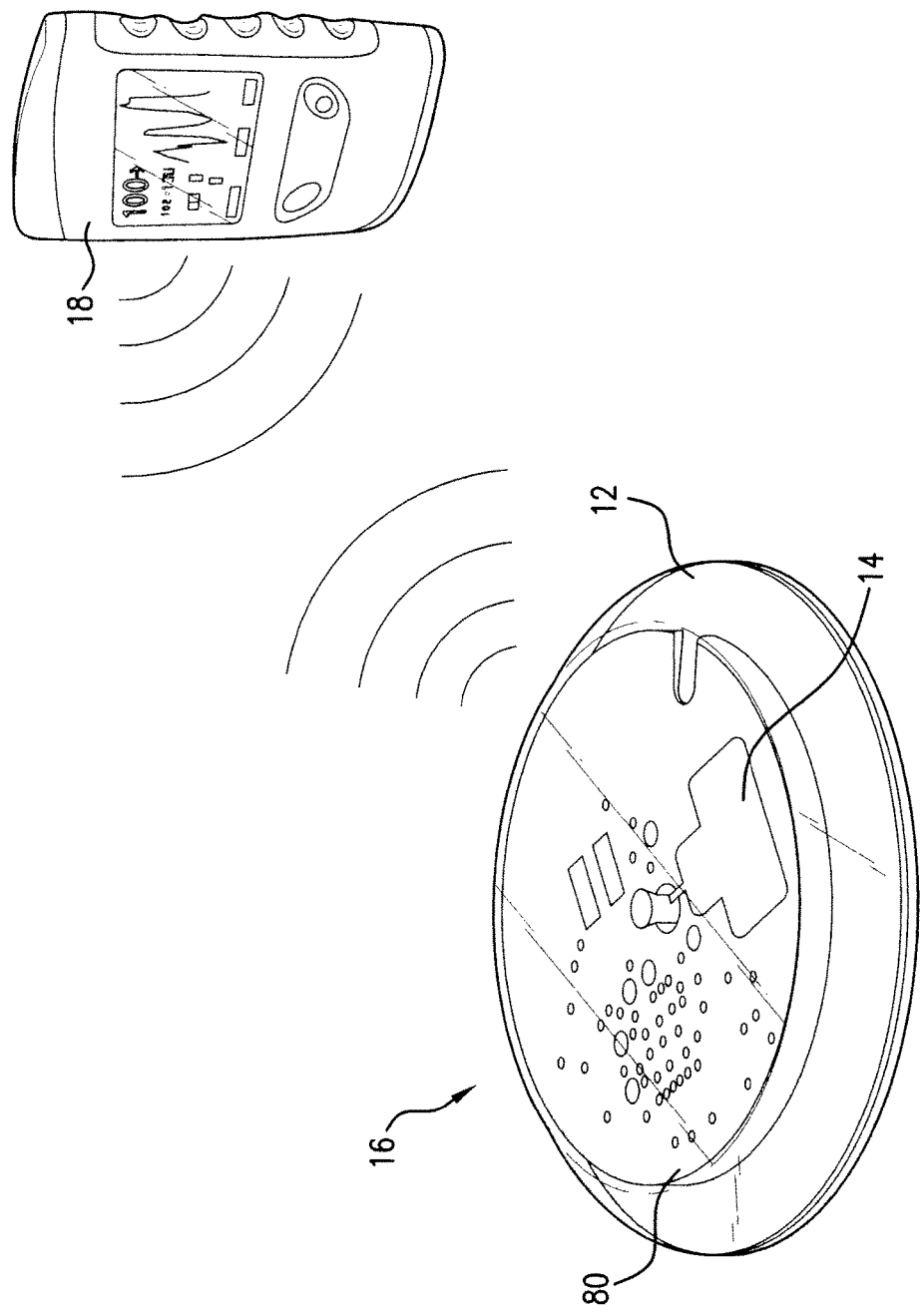
FIG. 9 is a schematic view of the system in accordance with one embodiment of the disclosed subject matter.

As illustrated in FIG. 9, the on-body unit 16 communicates with the monitor unit 18. Such communication may be one-way communication, e.g., from the on-body unit 16 to the monitor unit 18. In some embodiments, the communication may be two-way, e.g., both from the on-body unit 16 to the receiving unit 18 and from the receiving unit 18 to the on-body unit 16. In such cases, the receiving unit 18 may also be referred to herein as a display unit, transceiver or handheld unit. Communication between the on-body unit 16 and monitor unit 18 may occur via RF communication, inductive coupling, direct wired connection, etc.

Insertion Assembly

An insertion assembly is provided, which is used to install a medical device to the subject. In some embodiments, the insertion assembly includes an inserter and the medical device itself. The inserter can be configured to insert various medical devices to the subject, such as for example, an analyte sensor, an infusion set, a cannula, or a lancet. In some embodiments, the inserter can be configured to install a combination of such devices, e.g., a combined sensor/infusion set, etc. In certain embodiments, a given inserter can be configured to install a first device and a second device at different times. For example, an inserter may be modifiable to be used with more than one medical device, include more than one type of medical device, e.g., by attaching an adapter and/or removing detaching a portion of an inserter. The inserter can install the medical device transcutaneously in, under, or through the skin of the subject; or subcutaneously; or placed on the surface of the skin. The medical device can include features or structures, e.g., barbs, tabs, adhesive, etc., to maintain the device in position with respect to the skin after insertion.

In other embodiments, the insertion assembly includes an inserter, a medical device, such as an analyte sensor, and a mount for supporting the medical device at least partially in or on the skin of the subject. The mount may be inserted simultaneously with the medical device by the inserter. In other embodiments, the mount is installed after or before installation of the medical device. In such case the mount may be applied by the inserter or separately. The mount may include features or structures to maintain the sensor in position with respect to the skin after insertion.

In further embodiments, the insertion assembly includes an inserter, an analyte sensor, a mount, and a power supply. The mount and power supply may be inserted simultaneously with the analyte sensor by the inserter. In other embodiments, the mount and battery are installed after or before installation of the analyte sensor. In such case the mount and/or power supply may be applied by the inserter or separately.

In still further embodiments, the insertion assembly includes an inserter, a medical device such as an analyte sensor, a mount, and electronics. The mount and electronics may be inserted simultaneously with the analyte sensor by the inserter. In other embodiments, the mount and electronics are installed after or before installation of the analyte sensor. For example, the mount and the analyte sensor may be installed by the inserter, and the electronics may be subsequently installed. In other embodiments, the mount is installed, followed by insertion of the analyte sensor by the inserter, and further followed by installation of the sensor. In other embodiments, the mount and electronics are installed first, and the analyte sensor is subsequently installed.

In some embodiments, the electronics provide a voltage or current to the analyte sensor. In some embodiments, the electronics processes signals provided by the analyte sensor. In further embodiments, the electronics may include communication functionality for providing a signal relating to the signal provided by the analyte sensor to a further component, such as, e.g., a monitor unit, a handheld unit, a meter, a display unit, a computer, or other component. In some embodiments, communications circuitry, such as RFID antenna or communications circuitry is provided.

The inserter can include a plurality of different components. For example, the inserter may include one or more components for advancing a sharp towards the skin of the subject. The sensor and associated electronics and/or mounting structure may be supported by a support structure, such as a carriage. A driver may be provided for advancing the sharp and/or the analyte sensor/support structure. In some embodiments, the actuator is coupled to the sharp and/or support structure, such that manual force and speed applied by the user to the actuator is transferred to the sharp and/or support structure.

The inserter can also include one or more components for retracting the sharp, while allowing the analyte sensor and optional mount and/or electronics to remain to the subject. The components for retracting the sharp can include a retractor. It is understood that the retractor and the actuator may be the same structure or include some common components. In some embodiments, the retractor is directly or indirectly coupled to the sharp such that the manual force applied by the user is transferred from the retractor to the sharp to retract the sharp from the skin. In other embodiments, a drive assembly may be provided to retract the sharp. For example, the drive assembly may include a spring, motor, hydraulic piston, etc., to retract the sharp away from the skin of the subject. The drive assembly may also include a linear drive component.

In some embodiments, the retractor withdraws the sharp upon actuation by the user. In such cases, the user actuates the retractor when it is desired to withdraw the sharp. For example, the retractor may include a release switch. Upon activation of the release switch, the drive assembly, e.g., the spring or other driver, retracts the sharp from the skin. In other embodiments, the retractor and the actuator comprise common components. After activating the actuator to advance the sharp and the analyte sensor, the user releases the actuator, which allows the drive assembly to withdraw the sharp from the skin.

In some embodiments, the retractor withdraws the sharp without further user interaction after actuation of insertion. For example, the inserter may include features or components which automatically retract the sharp upon advancement of the sharp and support structure by a predetermined amount. Inserter devices, in which no further action by the user is required to initiate withdrawal of the sharp after insertion, are referred to herein as having "automatic" withdrawal of the sharp.

Inserter Devices

Figure 10:
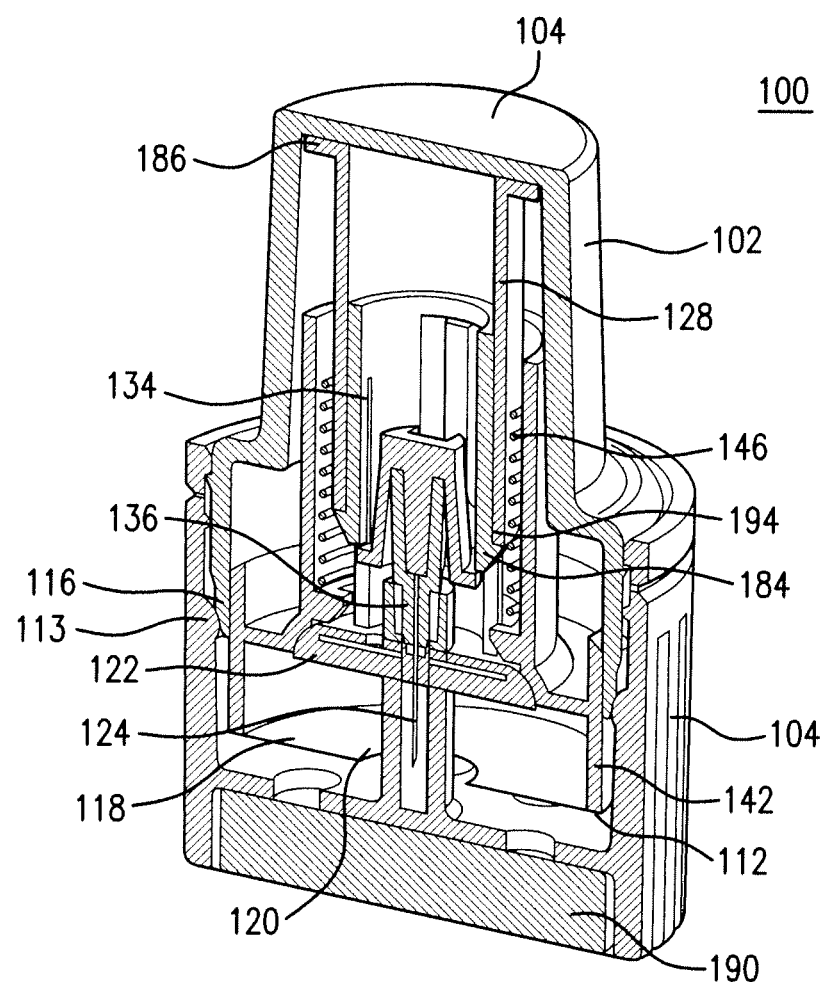
FIG. 10 is a sectional, perspective view of another embodiment of an inserter in accordance with the disclosed subject matter.

An inserter 100 in accordance with an exemplary embodiment is illustrated in FIG. 10. Inserter 100 includes a handle 102 and a removable distal cap 104. The cap 104 may maintain a sterile, contaminant-free environment for the medical device and sharp housed therein. As illustrated in FIGS. 10-16, distal cap 104 is secured to handle 102, e.g., by use of one or more mating members, e.g., threads 110 and 111, or hooks, tape, and the like. Inserter 100 includes a base 142 which defines a distal, substantially planar surface 112 for placement on the skin S of a subject, and in other embodiments may be a curved or inclined surface, e.g., a concave or convex surface. Inserter 100 may be utilized to advance a medical device into the skin of the subject, e.g., an analyte sensor, and infusion set, etc. In some embodiments, handle 102 is advanced relative to base 142 in order to advance the medical device into the skin of the patient, as will be described in greater detail herein.

The components of inserter 100 are illustrated in FIGS. 11-27. As illustrated in FIG. 11, handle 102 includes a contact surface 114 for contact by a user to insert and install the sensor housing 122 and sensor 14. Threads 110 are provided on handle 102 for attachment to cap 104 via threads 111 (as illustrated in FIGS. 12-13). Cap 104 can include an upwardly extending boss 125 to assist positioning of the sharp 124. The distal portion of cap 104 includes a recess 115 for retaining a desiccant 190 therein. In some embodiments, a silica gel or molecular sieves may be used. Such material can be in either in granular form (pellets) or pressed into tablets. In some embodiments, silica gel tablets are used.

Cap 104 is provided with one or more apertures 117, which allows for passage of air to the desiccant 190 to remove moisture from the interior of the inserter 100. Cap 104 includes an annular ridge 113 which engages the distal edge portion 116 of handle 102. In some embodiments, annular ridge 113 prevents distal movement of handle 102 (as well as sharp 124) when cap 104 is attached to handle 102.

Figure 14:
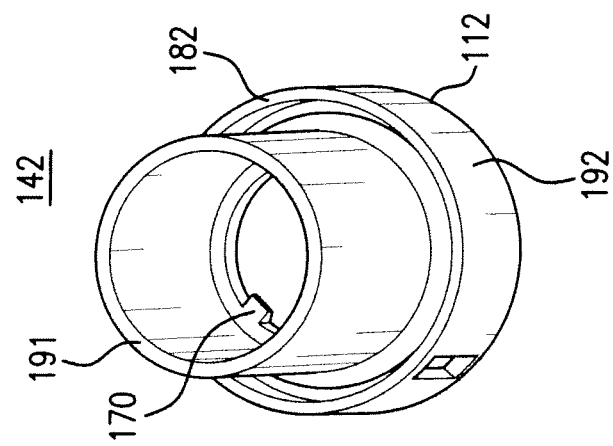
Figure 29:
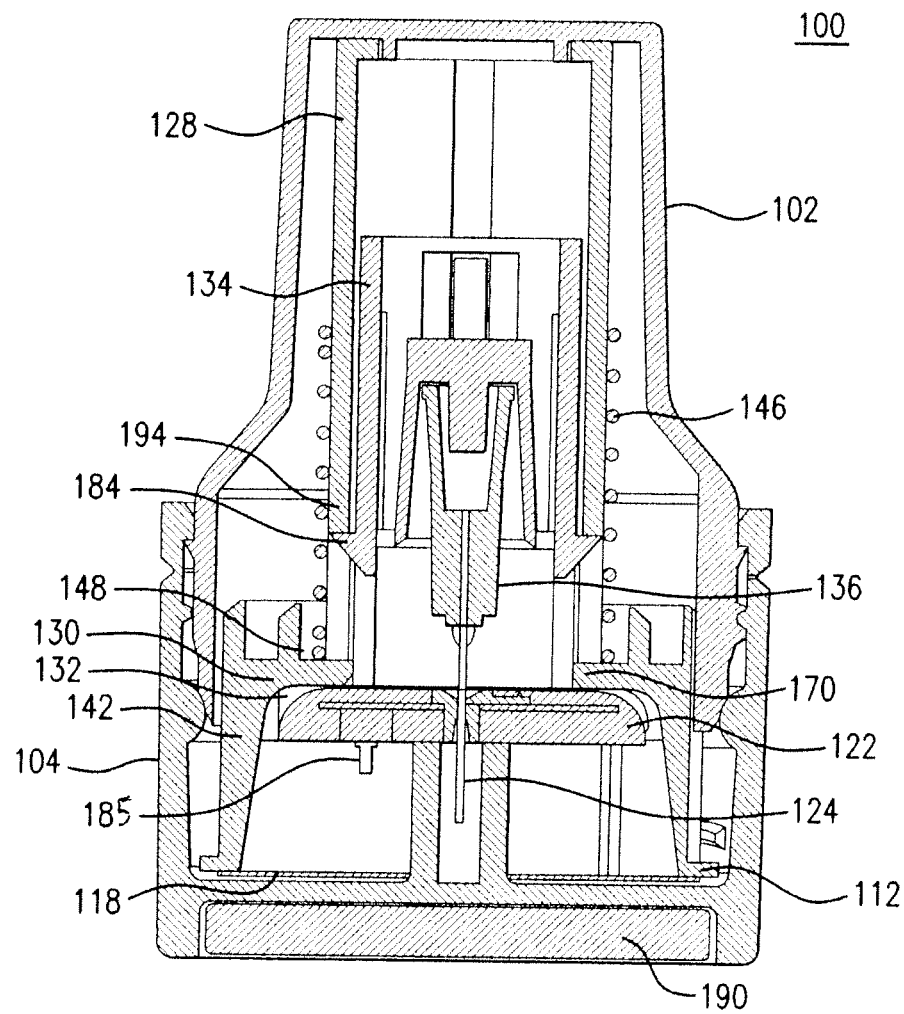

Base 142, as illustrated in FIGS. 10 and 14, includes a distal sheath portion 192, which shields sharp 124 prior to deployment and a distal rim 112 having a substantially planar surface configuration to rest on the subject's skin. Base 142 also includes side walls 191, which along with inner rail 128 defines a recess for retraction spring 146. Base 142 provides a spring floor 148, as illustrated in FIG. 29.

Figure 16:
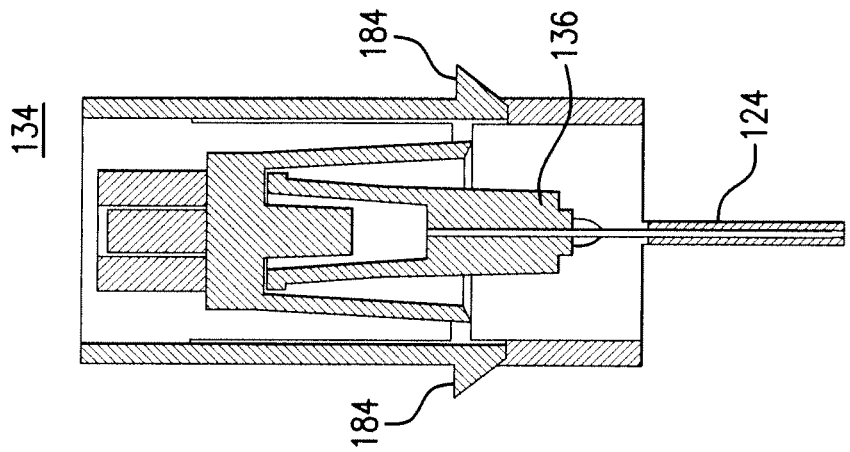
FIG. 16 is a sectional view of the component of FIG. 14 in accordance with the disclosed subject matter.
Figure 15:
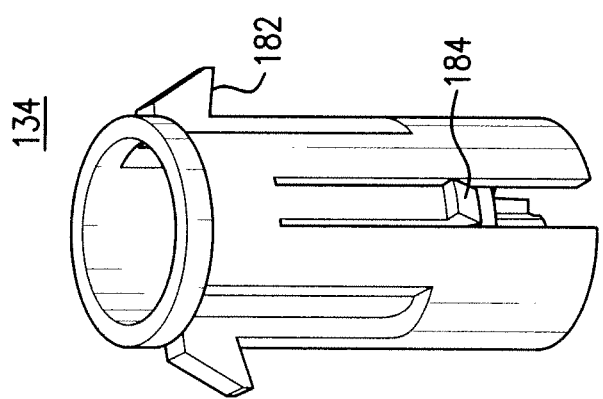
FIGS. 14-15 are a perspective views of components of the inserter of FIG. 10 in accordance with the disclosed subject matter.

Support member or shuttle 134, as illustrated in FIGS. 15-16, supports needle hub 136, from which sharp 124 extends longitudinally within the inserter 100. In some embodiments, the sharp is supported at an oblique angle, e.g., between about 0° and about 90° with respect to the skin surface. Needle hub 136 can be secured to shuttle 134 via an interlocking O-ring configuration, adhesive, or other techniques known in the art. In some embodiments, sharp 124 is a solid needle. In some embodiments, sharp 124 is provided with a substantially cylindrical configuration defining an interior bore, e.g., a rigid cannula or a hypodermic-style needle.

Needle hub 136 is further illustrated in FIGS. 17-18. Needle hub 136 supports sharp 124, having a sharpened distal portion 160. In some embodiments, as discussed herein, a longitudinal wall opening or gap 162 is provided in at least a portion of the wall of the sharp 124. The length N of the gap 162 is selected to be commensurate with the length of the insertion portion 30 through to the proximal retention portion 48 of the sensor, or about 5 mm, or about 10 mm, or about 15 mm, or about 20 mm. The length L of the sharp 124 may be about 5 mm, or about 10 mm, or about 20 mm, about 30 mm, or about 50 mm, and is selected based upon the desired depth of the insertion portion 30 of the sensor 14.

Figure 20:
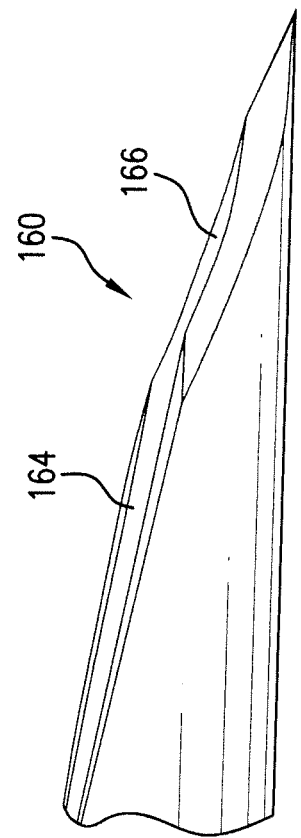
FIG. 20 is a side view of a sharp in accordance with one embodiment of the disclosed subject matter.
Figure 19:
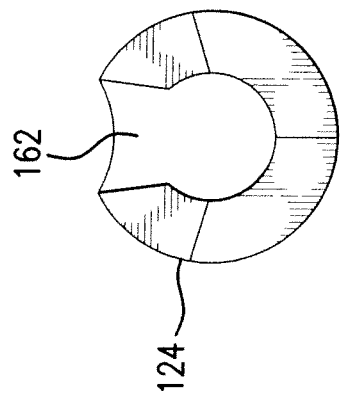
FIG. 19 is a distal end view of a sharp in accordance with one embodiment of the disclosed subject matter.
Figure 21:
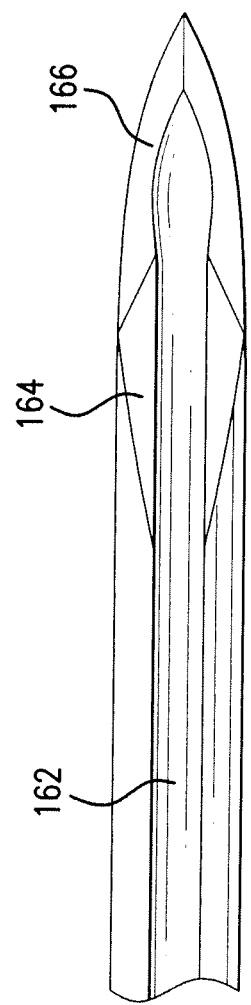
FIG. 21 is a side view of a sharp in accordance with one embodiment of the disclosed subject matter.

The distal portion 160 of sharp 124 is illustrated in greater detail in FIGS. 19-21. As illustrated in FIG. 19, sharp 124 has a substantially "C"- or "U"-shaped profile in this embodiment, but may have other configurations, e.g., substantially "V"-shaped. A longitudinal gap 162 is provided in the wall of the sharp 124. FIG. 20 illustrates distal portion 160 is provided with an angled tip. In some embodiments, the angled tip may be provided with a first angled tip portion 164 and a second steep-angled tip portion 166. The exemplary configuration, which includes multiple edges and faces, provides a sharp point to reduce penetration force, trauma, and bleeding for the subject. The distal section of the sensor body has a width sized to fit within the notch 162 of the insertion sharp 124 having a diameter less than about 22 to about 24 gauge, in certain embodiments the sharp is 25 gauge. In some embodiments, sharp 124 is a fabricated from a sheet of metal, and folded into a substantially "V" or "U" or "C" configuration in cross-section. In some embodiments, a laser is used to form the wall opening or gap 162.

Figure 22:
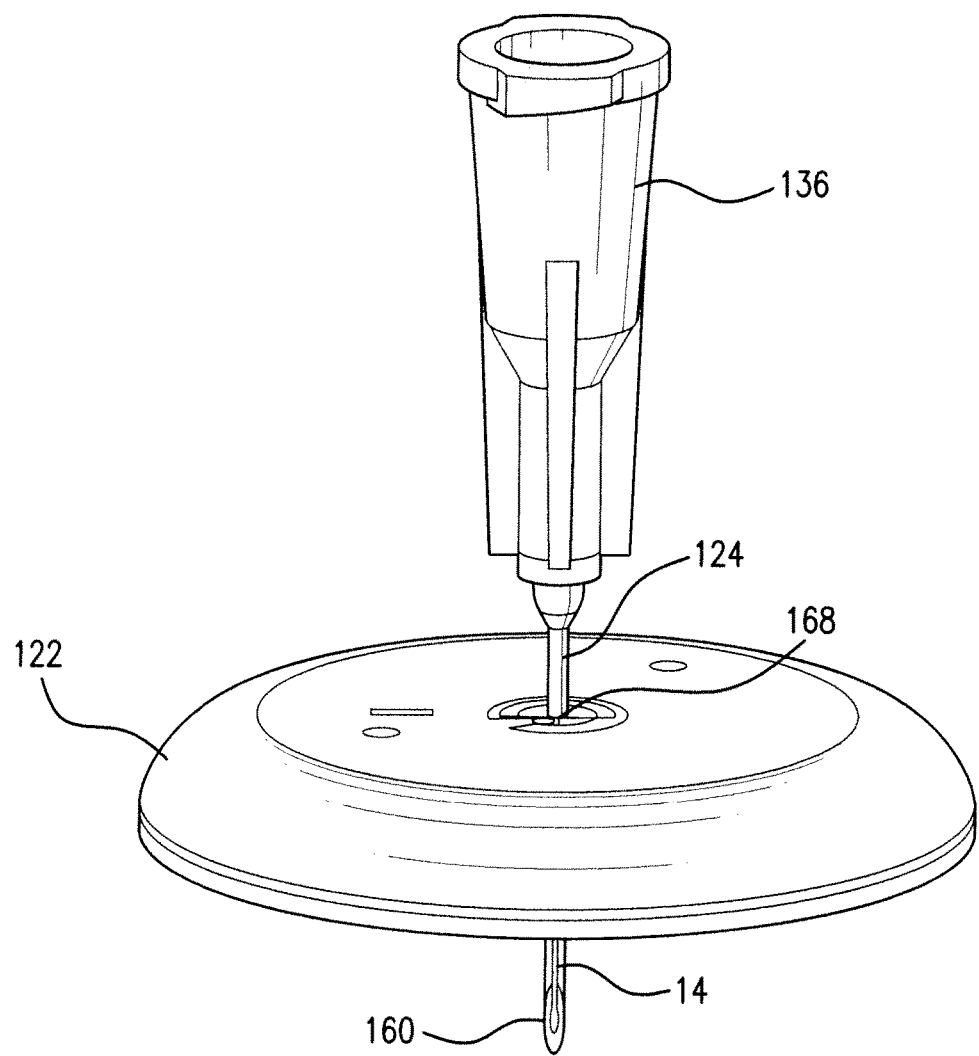
FIG. 22 is a perspective view with parts of an inserter in accordance with one embodiment of the disclosed subject matter.
Figure 23:
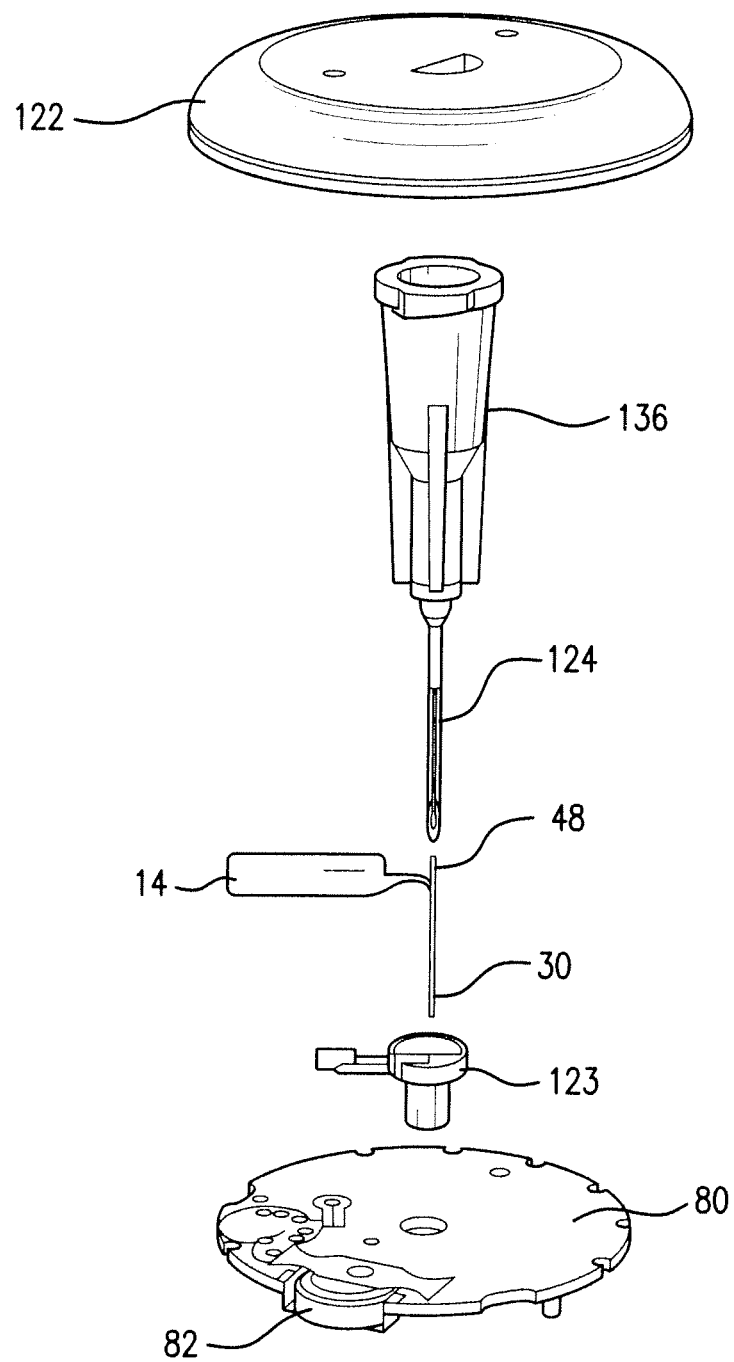
FIG. 23 is a perspective view with parts separated of an inserter in accordance with one embodiment of the disclosed subject matter.

FIGS. 22-23 illustrate the position of sensor housing 122 with respect to the needle hub 136 and sharp 124. As illustrated in FIG. 22, the sharp 124 extends through an aperture 168 in the sensor housing 122. The distal portion of sensor 14 is positioned with the sharp 124. As further illustrated in FIG. 23, electronics 80 (e.g., a printed circuit board containing ASIC electronics) and sensor hub 123 are positioned within sensor housing 122. A power supply 82, such as a battery, e.g., a single use disposable battery, or rechargeable battery, is provided. In some embodiments, the active operational life of the battery may exceed the active operational life of the sensor 14.

Figure 24:
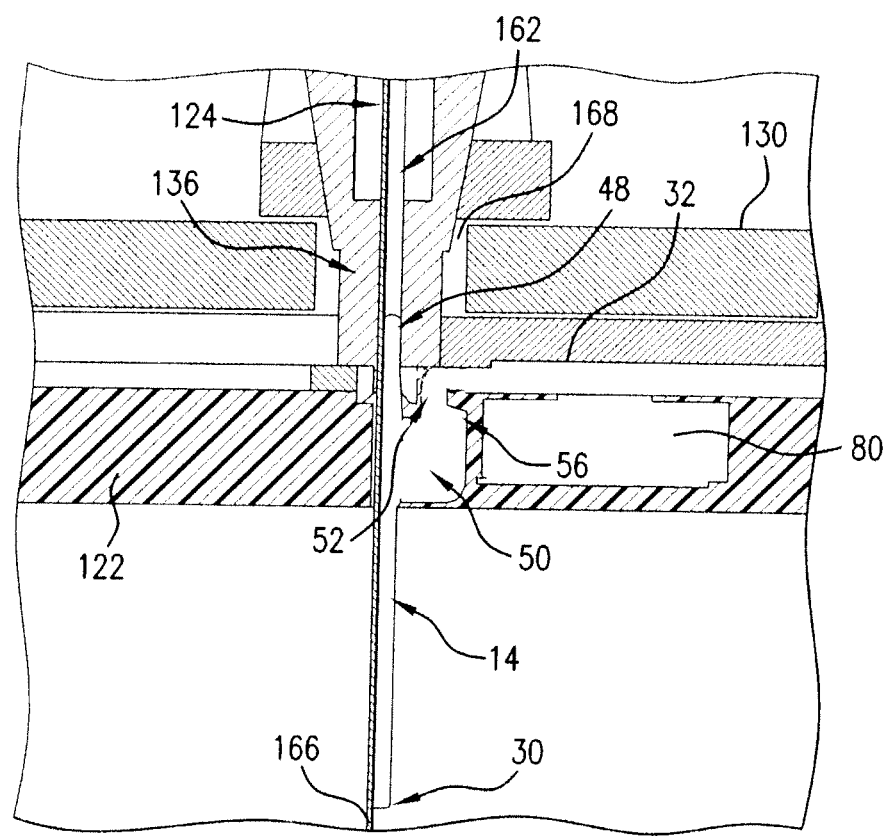
FIG. 24 is an enlarged sectional view with parts separated of an inserter in accordance with one embodiment of the disclosed subject matter.

FIG. 24 illustrates in cross-section the orientation of the sensor housing 122 with respect to the sharp 124 of inserter 100. As discussed herein, sensor 14 is disposed in a substantially bent configuration, such that a portion of the sensor, e.g., the insertion portion 30 and the proximal retention portion 48 are substantially vertical (e.g., substantially aligned with the longitudinal axis of the inserter 100 and substantially perpendicular to the skin surface) and the contact portion 32 (shown in profile) is oriented in a substantially horizontal configuration, and in electrical contact with the data processing unit electronics, such as circuit 80. The sensor tab 50 can be encased in the plastic of the sensor housing 122 (e.g., "overmolded") and secured in place. The notch 56 provides further stability to the sensor 14, e.g., by allowing the sensor tab 50 to be encased by the material of the sensor housing 122, and further provides a means for vertically orienting the sensor 14 during mounting, e.g., by allowing vertical positioning of the notch 56 with respect to a vertical landmark of the housing 122.

The sensor 14, mounted with the sensor housing 122, is disposed within the concave recess in the carriage 130. In the initial configuration of the inserter 100 (see, e.g., FIGS. 10 and 28-29) the sharp 124 extends through a longitudinal aperture 168 formed in a carriage 130. In some embodiments, the aperture 168 is appropriately sized, such that neither the sharp 124 nor needle hub 136 is in contact with the carriage 130. Accordingly, the needle hub 136 (and sharp 124) on the one hand, and the carriage 130 and the sensor housing 122, on the other hand, move simultaneously but independently from one another. In other embodiments, a friction fit may be provided between the aperture and the sharp.

The insertion portion 30 and proximal retention portion 48 of the sensor 14 are disposed within a longitudinal bore 162 within the sharp 124. (See, e.g., FIG. 19) The proximal retention portion 48 is disposed within the longitudinal bore of the sharp and provides additional stability to the mounting of the sensor 14 within the sharp 124. The longitudinal wall gap or opening 162 of sharp 124 is aligned with the sensor 14, such that the tab 50 and the contact portion 32 extend laterally outward from the sharp 124.

Figure 26:
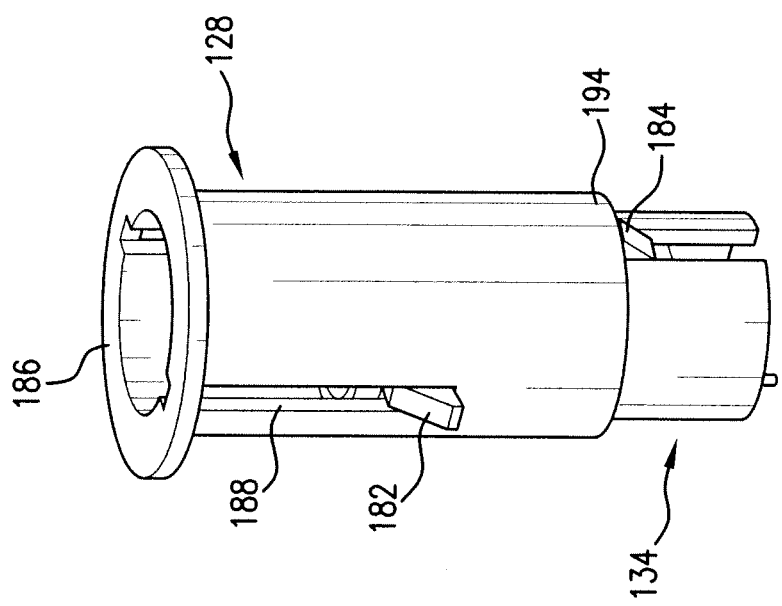
FIGS. 25-27 are perspective views of components of the inserter of FIG. 10 in accordance with the disclosed subject matter.
Figure 25:
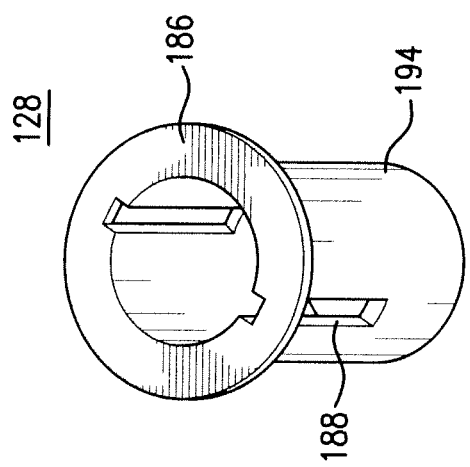

With continued reference to FIGS. 15 and 16, shuttle 134 includes wings 182 and resilient distally-extending fingers 184. Inner rail 128 is illustrated in FIG. 25. As illustrated in FIG. 26, shuttle 134 is sized and configured for slidable movement within inner rail 128. Wings 182 of shuttle 134 are configured for slidable movement within axial notches 188 of inner rail 128. When fingers 184 of shuttle 134 are disposed in their normally biased outward position, fingers 184 engage the lower surface 194 of inner rail 128. In the configuration illustrated in FIG. 26, shuttle 134 is locked with respect to inner rail 128. As will be discussed herein, fingers 184 may be biased radially inward to allow upward movement of shuttle 134 relative to inner rail 128.

As illustrated in FIG. 10, inner rail includes an upper surface 186 for engagement with handle 102. In some embodiments, surface 186 is adhered or otherwise fixed to handle 102.

Figure 27:
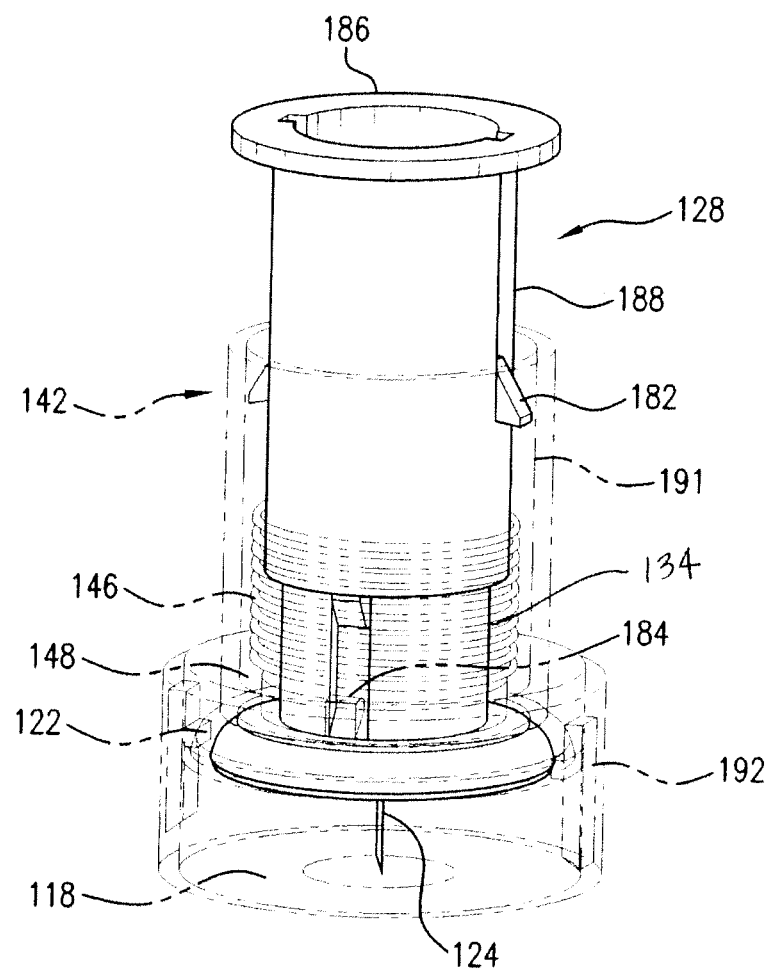

The relationship of inner rail 128, shuttle 134 and base 142 is illustrated in FIG. 27. In an initial configuration, inner rail 128 and shuttle 134 are in a locked relationship by engagement of wings 182 and fingers 184. Inner rail 128 and shuttle 134 are axially movable within base 142. Spring 146, which is secured between spring floor 148 of base 142 and wings 182 of shuttle 134 biases the inner rail 128 and shuttle 134 in a proximal (upward) direction.

Figure 28:
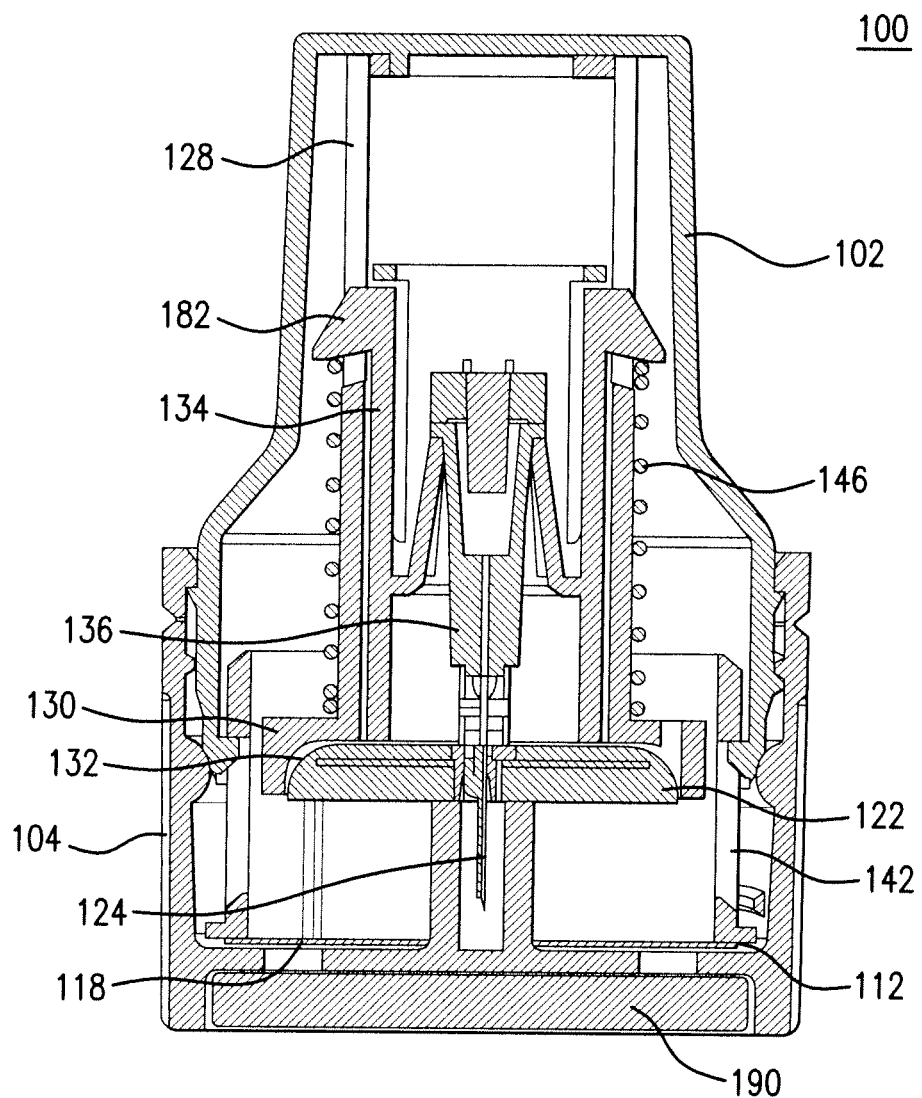
FIGS. 28-31 are sectional views of the inserter of FIG. 10 in accordance with the disclosed subject matter.

Inserter 100 is illustrated in section in FIGS. 28-29 prior to use in a sensor predeployment position. Cap 104 is attached to the distal portion of inserter 100, via inter-engagement of threads 110 and 111.

As illustrated in FIG. 28, the inserter 100 includes an initial configuration in which the handle 102 is disposed in a proximal position with respect to the base 142. In such configuration, the sharp 124 is disposed in a configuration spaced apart from an aperture of the adhesive layer 118.

Figure 30:
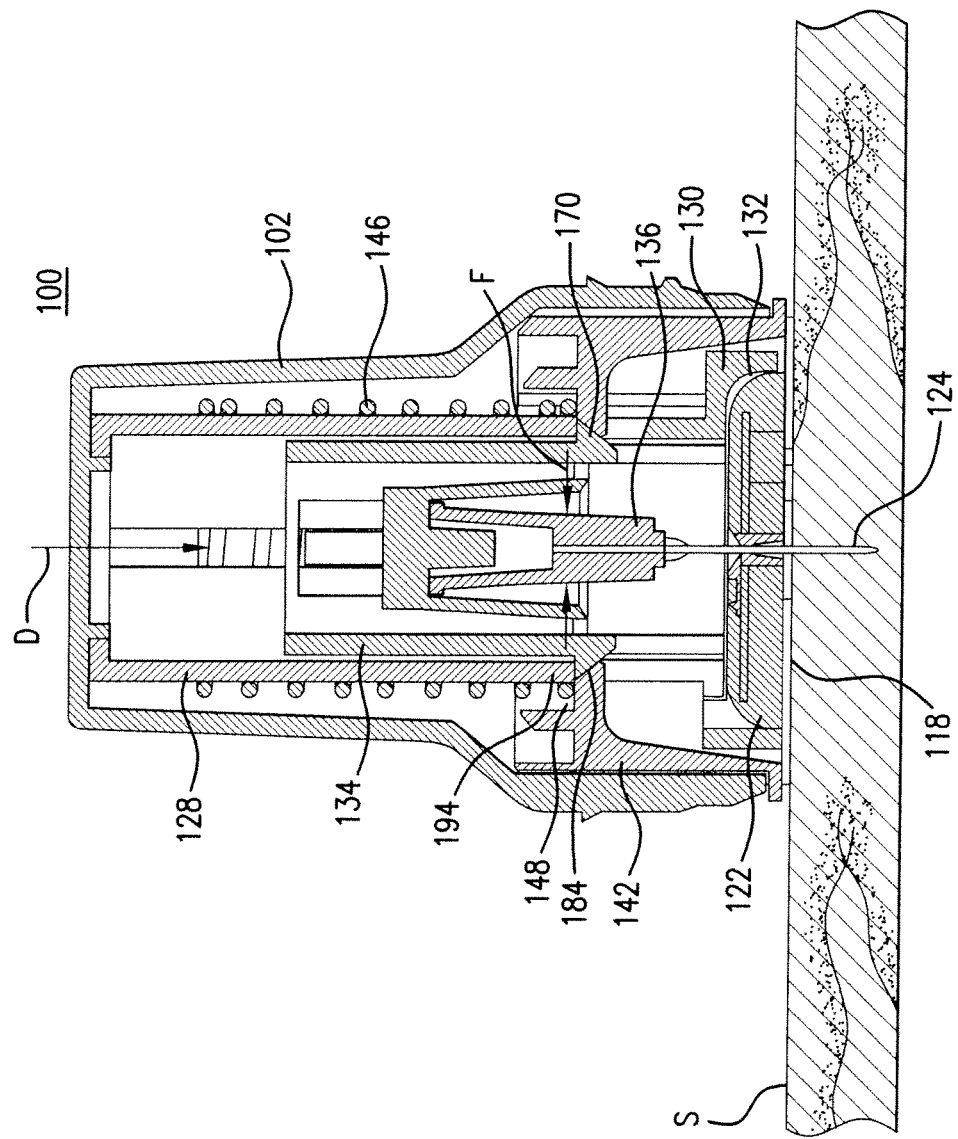

As illustrated in FIG. 30, inner rail 128 includes a carriage 130. In a sensor insertion position, the handle 102 is depressed downward (arrow D) against the bias of spring 146, the inner rail 128 moves downwardly with the carriage 130 and the sensor housing 122. Shuttle 134 supports needle hub 136, from which sharp 124 extends longitudinally within the inserter 100. Initially shuttle 134 is coupled to inner rail 128 via inter-engagement of fingers 184 of shuttle 134 with distal surface 194 of inner rail 128, and both shuttle 134 and inner rail 128 move distally together as a unit.

As the sharp 124 is urged distally (FIG. 30), it carries the sensor insertion portion 30 of sensor 14 into the subcutaneous portion of the subject's skin S and into contact with the interstitial fluid. As carriage 130 reaches a distal position, the distal surface of the sensor housing 122 engages the upper surface of adhesive pad 118, thereby becoming adhered to the skin surface S of the subject.

Flanges 170 on base 142 engage fingers 184 of shuttle 134. Fingers 184 are pivoted or bend inwards by contact with flanges 170 (as indicated by arrows F).

Figure 31:
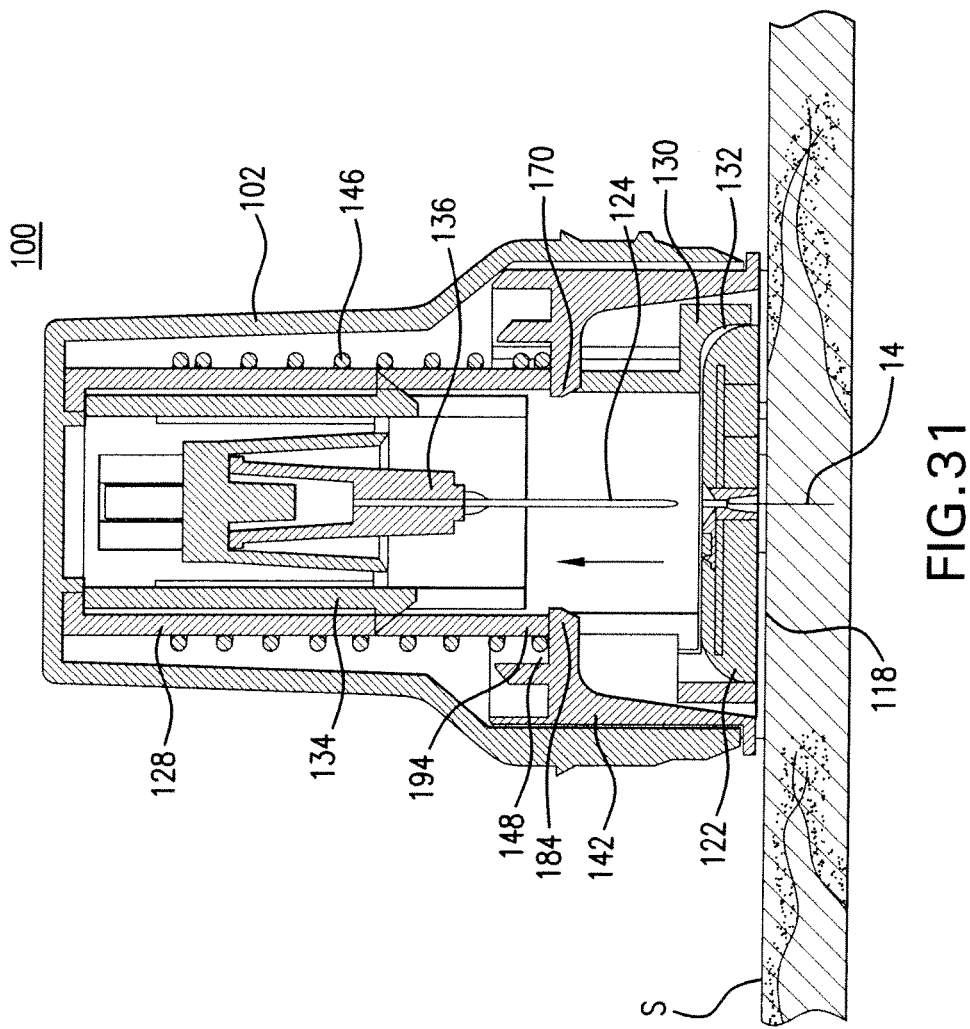

As illustrated in FIG. 31, such pivoting of fingers 184 causes fingers 184 to become disengaged from distal edge 194 of inner rail 128. Shuttle 134 is thereby disengaged from inner rail 128. Disengagement of the shuttle 134 from the inner rail 128 permits the spring 146 to expand, thereby advancing the shuttle 134 to a proximal position, and withdrawing the sharp 124 from the sensor 14 and the skin S of the subject, while leaving the sensor 14 in the skin. Once the sharp has been withdrawn from the subject, it is no longer accessible from the distal portion of the inserter 100, which prevents accidental needle sticks. When the carriage 130 reaches the distal position in which flanges 170 engage fingers 184 of needle shuttle 134, needle shuttle 134 withdraws needle 124 automatically without further input from the user.

Prior to activation of the integrated sensor 14 and sensor electronics assembly 16 for use, there may be a period of time from the manufacturing that the assembly 16 may be in a "sleep" or "idle" mode. With a power supply such as a battery integrated within the assembly, for reasons including cost optimization and prolonging shelf life, embodiments of the present disclosure include systems that are activated merely by positioning the sensor 14 and electronics unit 16 on a skin surface as described above, i.e., no additional action may be required of the user other than applying a force to housing 122. As such, insertion of the sensor 14 and/or mounting of the housing 122 causes activation of the electronics 80. In certain embodiments, activation switch configurations are included which may be configured to be triggered, for example, by the insertion device activation, thereby turning on the integrated sensor and sensor electronics assembly into an active mode.

As illustrated in FIG. 29, inserter 100 is also provided with a plunger switch 185, which provides automatic activation of the electronics 80 of the data processing unit 12. In some embodiments, the plunger switch 185 is a longitudinally slidable member disposed on the distal surface of the sensor housing 122. When the sensor housing is advanced proximally, it engages the adhesive pad 118, or alternatively the skin surface of the subject. Upon such engagement, the plunger switch 185 is moved axially (proximally) with respect to the housing 122. The plunger switch in the proximal position is shown in FIG. 30, for example. Such axial movement is used to activate the sensor electronics 80. In some embodiments, the plunger switch is spring biased. Accordingly, as long as the sensor housing is maintained in a fixed relationship with the adhesive pad 118 against the bias, electronic activation is maintained. If the sensor housing is removed from the adhesive or the skin, the plunger switch moves with the bias, and the electronics are deactivated. In other embodiments, the plunger switch provides a one-time activation of the electronics. In such cases, once the electronics are activated, the sensor housing is not required to remain in contact with the adhesive or the skin in order to maintain activation.

Figure 32:
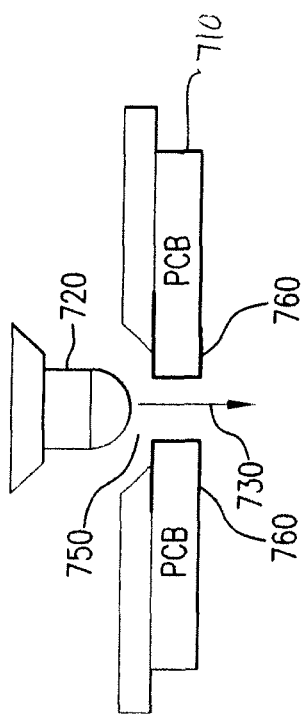
FIGS. 32-33 illustrate a power supply switch mechanism including conductive plug of the on-body integrated sensor and sensor electronics assembly in accordance with embodiments of the disclosed subject matter.
Figure 33:
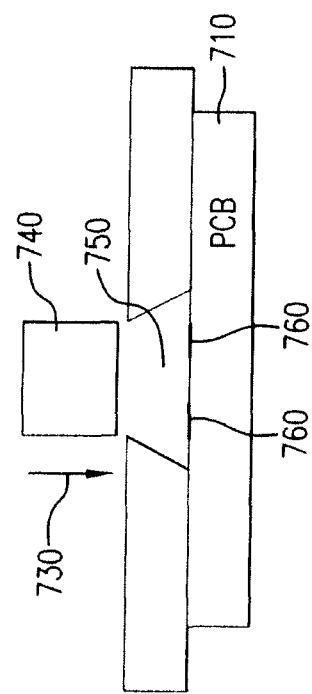

As illustrated in FIGS. 32-33, embodiments of a power supply switch mechanism include conductive plugs of the on-body integrated sensor and sensor electronics assembly 16 in accordance with the present disclosure. FIGS. 32-33 illustrate enlarged sectional views of sensor housing 122. As shown, the sensor electronics assembly circuit board 710 may be provided with a physical gap 750 that breaks the electrical circuit between the power supply (e.g., battery) and the other circuitry of the sensor electronics assembly.

In one embodiment, when the predetermined force is applied on the insertion device 100 as discussed above, a conductive portion 720 provided within the housing 122 of the sensor electronics may be moved in a direction as shown by arrow 730 such that electrical contact is established in the physical gap 750 on the circuit board, by for example, the conductive portion 720 coming into physical contact with the conductive portions 760 of the circuit board 710. In this manner, in one embodiment, the electrical path from the power supply and the remaining circuitry on the circuit board of the sensor electronics is completed, thereby powering the sensor electronics.

By way of another example, referring to FIG. 33, the conductive portions 760 of the circuit board are provided on the board itself, and the conductive plug 740, for example, when pushed into the cavity 750, establishes electrical contact between the conductive portions 760 of the circuit board.

In one embodiment, as discussed above, the actuation of the insertion device 100 to position the sensor and sensor electronics assembly triggers the switch mechanism shown in FIGS. 32-33 by also moving the conductive portion 720 or the conductive plug 760 in the direction complimentary to the direction of the introducer movement, and thereby switching on the sensor electronics. Within the scope of the present disclosure, the activation of the sensor electronics by moving the conductive portion 720 or the conductive plug may include a separate procedure, where after positioning the sensor and the sensor electronics assembly on the skin surface, a predetermined force is applied on the housing of the integrated sensor 14 and sensor electronics assembly such that the desired movement of the conductive portion 720 or the conductive plug 760 may be achieved.

Figure 34A:
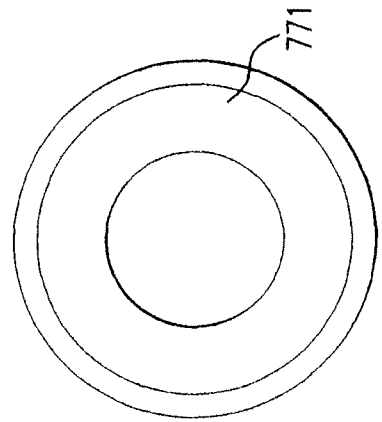
FIGS. 34A-36B illustrate a power supply switch mechanism including conductive pads on the on-body integrated sensor and sensor electronics assembly in accordance with embodiments of the disclosed subject matter.
Figure 34B:
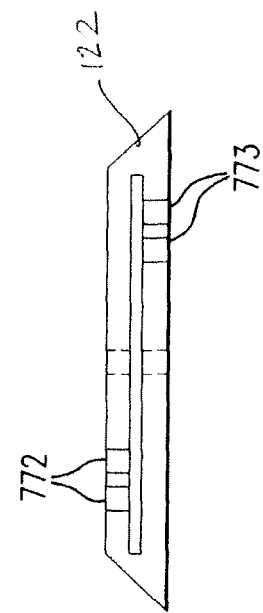

FIGS. 34A-36B illustrate another configuration of the power supply switch mechanism including conductive pads of the on-body integrated sensor and sensor electronics assembly in accordance with embodiments of the present disclosure. Referring to FIG. 34A, an exposed conductive ring 771 may be provided and configured to contact the surface of the circuit board in the sensor housing 122 (shown in cross section in FIG. 34B) such that, the insertion device activation positions the conductive ring 771 on the surface of the circuit board so as to complete the electrical contact of the sensor housing 122 (by for example, manual force applied on the insertion device placing the conductive ring in contact with the circuit board of the sensor electronics).

Figure 35A:
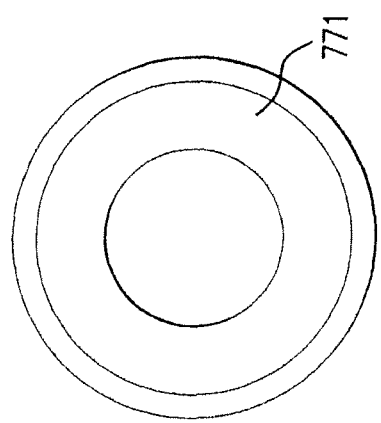
Figure 35B:
Figure 36A:
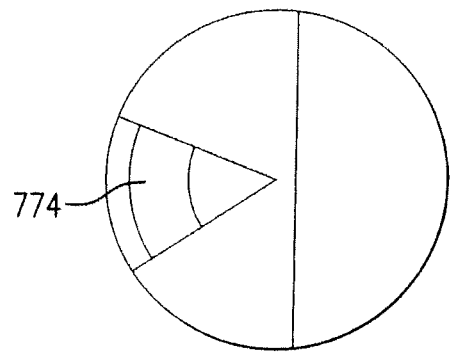
Figure 36B:
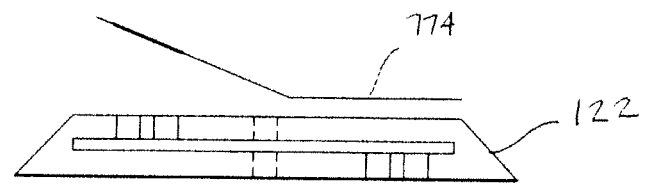

Referring to FIGS. 35A-B, in another aspect, electrical contact pads 772, 773 may be provided to the circuit board in the sensor housing 122 (shown in cross section in FIG. 35B, such that the mating of the contact pads with the conductive ring 771 switches on the sensor electronics device to provide power to the device from its power source. FIGS. 36A-B show yet another configuration of the switch activation mechanism in accordance with the present disclosure, where a portion of the conductive ring 774 is selectively positioned and provided to establish electrical contact in the sensor housing 122 (shown in cross section in FIG. 36B).

As discussed, each of the activation configuration described above includes a break in the circuitry from the power source such that the power supply is not drained when the device is not in use, and upon activation, the break in the electrical contact is completed, thereby powering the device and activating it for operation.

Figure 37:
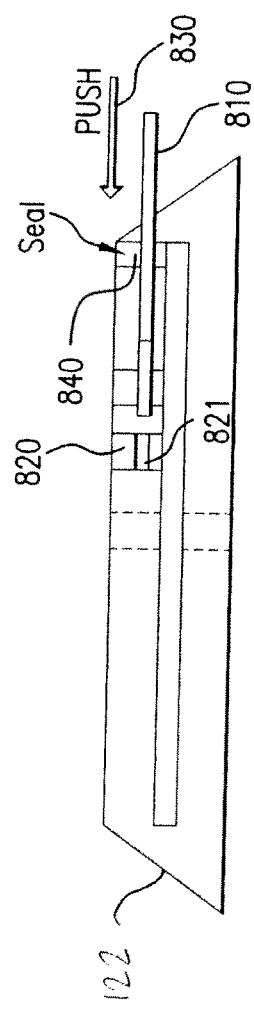
FIG. 37 illustrates a power supply switch mechanism including an internal switch with a push rod activation of the on-body integrated sensor and sensor electronics assembly in accordance with embodiments of the disclosed subject matter.

FIG. 37 illustrates a power supply switch mechanism including an internal switch with a push rod activation of the on-body integrated sensor and sensor housing 122 in accordance with embodiments of the present disclosure. As shown, in one embodiment, push rod 810 may be provided and positioned in the sensor electronics such that when a force is applied in the direction as shown by arrow 830, the push rod 810 is displaced in the same direction and completes the electrical contact between the two contacts 820, 821. In one aspect, the push rod 810 may be provided within a seal 840 such as an O-ring or similar components.

Figure 38:
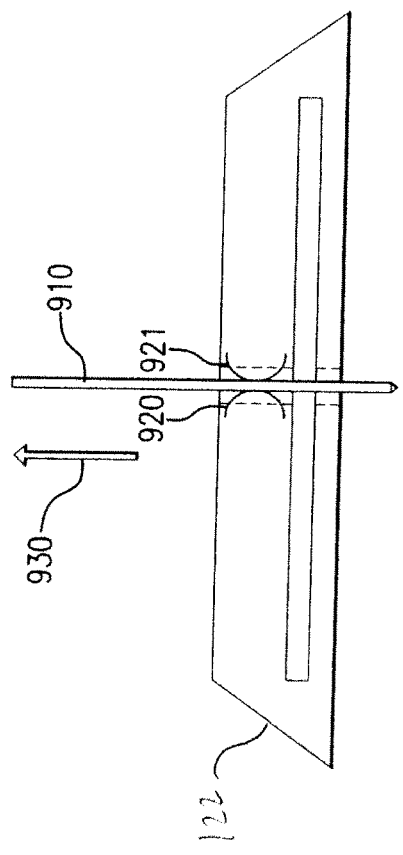
FIG. 38 illustrates power supply switch mechanism including introducer retraction trigger activation of the on-body integrated sensor and sensor electronics assembly in accordance with embodiments of the disclosed subject matter.

FIG. 38 illustrates power supply switch mechanism including introducer retraction trigger activation of the on-body integrated sensor and sensor housing 122 in accordance with embodiments of the present disclosure. As shown, a nonconducting needle or device 910 is provided to physically separate two electrical contacts 920, 921. Each of the electrical contacts 920, 921 is biased or spring loaded to be urged towards each other, physically separated by the nonconducting needle 910. Accordingly, when the nonconducting needle 910 is retracted or pulled away from the sensor electronics assembly in the direction as shown by arrow 930, the electrical contacts 920, 921 are configured to contact each other, thereby completing the break in the circuit and establishing electrical connection to activate the sensor electronics assembly. In one aspect, the nonconducting device or needle 910 may include, for example, but not limited to, glass, plastic or any other material suitable to separate two electrical contacts and provide insulation therebetween.

Figure 39:
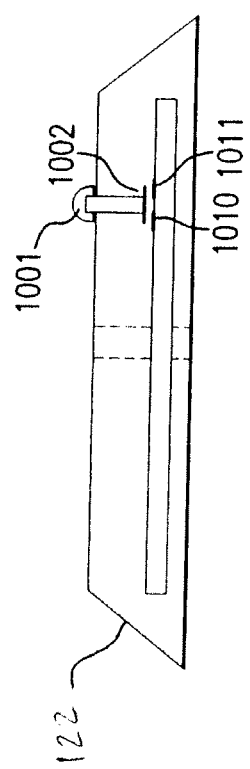
FIG. 39 illustrates a power supply switch mechanism with a contact switch of the on-body integrated sensor and sensor electronics assembly in accordance with embodiments of the disclosed subject matter.

FIG. 39 illustrates power supply switch mechanism with a contact switch of the on-body integrated sensor and sensor electronics assembly in accordance with embodiments of the present disclosure. As shown, in a further aspect, there is provided an electronic switch 1001 (that is configured to draw an insubstantial amount of power from the sensor electronics power supply), and when triggered, completes the break between the contacts 1010, 1011 by physically contacting the two contacts 1010, 1011 with the activation component 1002 that completes the circuit in the sensor electronics from its power supply such as battery to activate the device for operation.

FIGS. 40-41 illustrate a power supply switch mechanism with a battery contact locking mechanism of the on-body integrated sensor and sensor electronics assembly 122 in accordance with the present disclosure. Referring to FIGS. 40-41, in still another aspect, the battery contact of the sensor electronics may be provided with a barbed tab 1110. In post manufacturing shelf mode when the device is non-operational, the tab 1110 is positioned within the sensor electronics housing in the position as shown in FIG. 40 so that it is not in contact with the conductive contact 1120 of the sensor electronics circuit board. When in use as shown in FIG. 41, the tab 1110 may be biased such that it physically contacts the conductive contact 1120 on the circuit board, thereby closing the circuit to/from the battery/power source and thus activating or switching on the sensor electronics. As shown in the Figures, the tab 1110 may be configured that upon biasing to establish contact with the conductive contact 1120, it locks or latches with the conductive contact 1120 and the circuit board so as to maintain the electrical connection.

Figure 42:
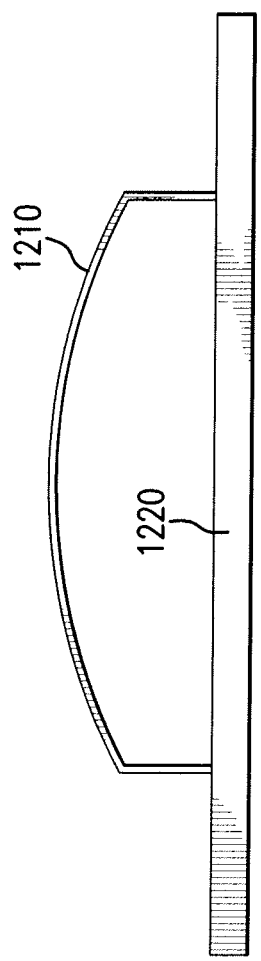
FIGS. 42-43 illustrate a power supply switch mechanism with a bi-modal dome switch of the on-body integrated sensor and sensor electronics assembly in accordance with embodiments of the disclosed subject matter.
Figure 43:
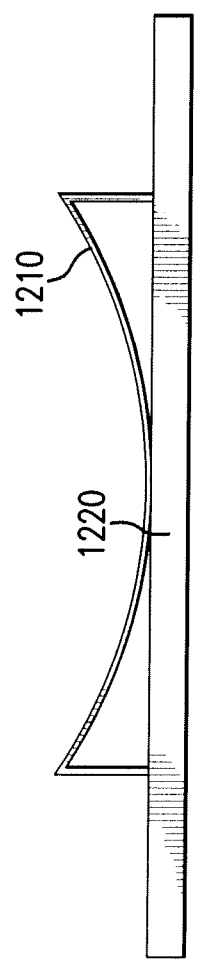

FIGS. 42-43 illustrate power supply switch mechanism with a bi-modal dome switch of the on-body integrated sensor and sensor electronics assembly in accordance with embodiments of the present disclosure. Yet in another embodiment, a bi-modal dome shaped switch 1210 is provided on the circuit board of the sensor electronics assembly such that, when pressed down (as shown in FIG. 42), the dome shaped layer 1210 (which may include, for example, a thin sheet metal dome) may be configured to retain the concave shape as shown in FIG. 43 and effectively closing the circuit on the circuit board at the contact point 1220. In one aspect, the dome shaped layer 1210 may be configured to shunt to short two or more electrical contacts at the contact point 1220 of the circuit board. Alternatively, the dome shaped layer 1210 may be connected to the circuit board such that one end of the dome shaped layer 1210 is in contact with one of the two or more open electrical contacts, and the depression of the dome shaped layer 1210 closes the circuit on the circuit board by physically contacting the other one or more of the open electrical contacts.

In the manner described above, in accordance with various embodiments of the present disclosure, sensor electronics activation switch configurations are provided that may be triggered or activated automatically or semi-automatically in response to the activation of the insertion device described above, or alternatively, may be separately activated by the user by, for example, depressing upon a portion of the housing or switch provided on the housing of the sensor electronics. Accordingly, power consumption may be optimized for the sensor electronics assembly while improving post manufacturing shelf life of the device prior to use or activation.

It is understood that the subject matter described herein is not limited to particular embodiments described, as such may, of course, vary. It is also understood that the terminology used herein is for the purpose of describing particular embodiments only, and is not intended to be limiting, since the scope of the present subject matter is limited only by the appended claims.

Additional detailed description of embodiments of the disclosed subject matter are provided in but not limited to: U.S. Pat. Nos. 7,299,082; 7,167,818; 7,041,468; 6,942,518; 6,893,545; 6,881,551; 6,773,671; 6,764,581; 6,749,740; 6,746,582; 6,736,957; 6,730,200; 6,676,816; 6,618,934; 6,616,819; 6,600,997; 6,592,745; 6,591,125; 6,560,471; 6,540,891; 6,514,718; 6,514,460; 6,503,381; 6,461,496; 6,377,894; 6,338,790; 6,299,757; 6,299,757; 6,284,478; 6,270,455; 6,175,752; 6,161,095; 6,144,837; 6,143,164; 6,121,009; 6,120,676; 6,071,391; 5,918,603; 5,899,855;

5,822,715; 5,820,551; 5,628,890; 5,601,435; 5,593,852; 5,509,410; 5,320,715; 5,264,014; 5,262,305; 5,262,035; 4,711,245; 4,545,382; U.S. Patent Publication No. 2004/0186365, published Sep. 23, 2004, now 7,811,231; U.S. Patent Application 61/238,646, filed Aug. 31, 2009, the disclosures of each of which is incorporated herein by reference.

What is claimed is:

1. An apparatus adapted to insert a sensor through the skin of a subject, the apparatus comprising:
   a sheath having a surface for placement on the skin of the subject;
   a handle movable relative to the sheath;
   an analyte monitoring assembly comprising the sensor;
   a sharp support adapted to support a sharp; and
   a spring in contact with a surface of the sharp support,
   wherein the apparatus is configured such that advancement of the handle, while the spring is in contact with the surface of the sharp support, advances the sharp support, the sharp, and the analyte monitoring assembly from a first position within the apparatus to a second position where at least a portion of the sensor is brought into contact with fluid in the subject, and
   wherein the spring is adapted to automatically retract the sharp support and sharp away from the skin with a force applied by the spring against the surface of the sharp support after the advancement of the handle.

2. The apparatus of claim 1, wherein the handle is at least partially disposed within the sheath.

3. The apparatus of claim 1, wherein the handle is at least partially disposed surrounding the sheath.

4. The apparatus of claim 1, wherein the sharp support is permanently fixed to the handle.

5. The apparatus of claim 1, further comprising a carriage adapted to releasably hold the analyte monitoring assembly.

6. The apparatus of claim 5, wherein the carriage is part of an inner rail that contacts a handle surface.

7. The apparatus of claim 5, wherein the apparatus is configured such that advancement of the handle, while the spring is in contact with the surface of the sharp support, advances the carriage, the sharp support, the sharp, and the analyte monitoring assembly from the first position to the second position.

8. The apparatus of claim 7, wherein apparatus is configured such that the spring automatically retracts the sharp support and sharp away from the skin and away from the carriage while the carriage releasably holds the analyte monitoring assembly.

9. The apparatus of claim 8, wherein the spring is positioned in contact with the surface of the sharp support and a surface of the carriage, and wherein the sharp support is automatically retractable by exertion of a force by the spring against the surface of the sharp support and the surface of the carriage.

10. The apparatus of claim 1, wherein the analyte monitoring assembly is adhesively securable to the skin.

11. The apparatus of claim 1, wherein the handle is advanceable by application of manual force to the handle.

12. The apparatus of claim 1, wherein the sensor is a glucose sensor.

13. The apparatus of claim 1, further comprising a removable cap.

14. The apparatus of claim 13, wherein the removable cap is adapted to removably couple with the handle.

15. The apparatus of claim 1, wherein the sharp support comprises a plurality of resilient extending fingers.

16. The apparatus of claim 1, wherein the analyte monitoring assembly comprises an aperture through which the sharp can pass.

17. The apparatus of claim 16, wherein the analyte monitoring assembly has a substantially circular profile.

18. The apparatus of claim 1, further comprising a hub coupled with the sharp.

19. The apparatus of claim 18, wherein the sharp support is coupled with the hub.

* * * * *